(12) United States Patent
Lu et al.

(10) Patent No.: US 9,796,784 B2
(45) Date of Patent: *Oct. 24, 2017

(54) METHODS AND COMPOSITIONS FOR THE GENERATION AND USE OF CONFORMATION-SPECIFIC ANTIBODIES

(71) Applicant: Beth Israel Deaconess Medical Center, Inc., Boston, MA (US)

(72) Inventors: Kun Ping Lu, Newton, MA (US); Xiao Zhen Zhou, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/325,013

(22) Filed: Jul. 7, 2014

(65) Prior Publication Data

US 2015/0038683 A1 Feb. 5, 2015

Related U.S. Application Data

(62) Division of application No. 13/504,700, filed as application No. PCT/US2010/054077 on Oct. 26, 2010, now Pat. No. 8,771,693.

(60) Provisional application No. 61/255,341, filed on Oct. 27, 2009.

(51) Int. Cl.
| | |
|---|---|
| A61K 38/06 | (2006.01) |
| A61K 38/08 | (2006.01) |
| C07K 7/00 | (2006.01) |
| A61P 25/28 | (2006.01) |
| C07K 16/40 | (2006.01) |
| C07K 14/47 | (2006.01) |

(Continued)

(52) U.S. Cl.
CPC .......... *C07K 16/40* (2013.01); *C07K 14/4711* (2013.01); *C07K 16/44* (2013.01); *G01N 33/573* (2013.01); *C07K 2317/14* (2013.01); *G01N 2333/99* (2013.01)

(58) Field of Classification Search
None
See application file for complete search history.

(56) References Cited

U.S. PATENT DOCUMENTS

| | | | |
|---|---|---|---|
| 4,489,078 A | 12/1984 | Temple, Jr. | |
| 4,591,588 A | 5/1986 | Wade | |
| 4,734,413 A | 3/1988 | Wade | |

(Continued)

FOREIGN PATENT DOCUMENTS

| | | |
|---|---|---|
| WO | WO-83/00229 A1 | 1/1983 |
| WO | WO-9607399 A1 | 3/1996 |

(Continued)

OTHER PUBLICATIONS

An et al., Retention of the Cis Proline Conformation in Tripeptide Fragments of Bovine Pancreatic Ribonuclease A Containing a Non-natural Proline Analogue, 5,5-Dimethylproline. J. Am. Chem. Soc. 1999, 121, 11558-11566.*

(Continued)

*Primary Examiner* — Daniel E Kolker
*Assistant Examiner* — Aurora M Fontainhas
(74) *Attorney, Agent, or Firm* — Clark & Elbing LLP; Kristin Bieker-Brady

(57) ABSTRACT

The present invention features methods and compositions for the generation and use of conformation-specific antibodies or fragments thereof.

20 Claims, 6 Drawing Sheets

(51) Int. Cl.
C07K 16/44 (2006.01)
G01N 33/573 (2006.01)

(56) References Cited

U.S. PATENT DOCUMENTS

| | | |
|---|---|---|
| 4,816,567 A | 3/1989 | Cabilly et al. |
| 5,530,101 A | 6/1996 | Queen et al. |
| 5,627,153 A | 5/1997 | Little, II et al. |
| 5,639,600 A | 6/1997 | McGrath et al. |
| 5,654,010 A | 8/1997 | Johnson et al. |
| 5,821,337 A | 10/1998 | Carter et al. |
| 5,952,467 A | 9/1999 | Hunter et al. |
| 5,972,697 A | 10/1999 | Hunter et al. |
| 6,054,297 A | 4/2000 | Carter et al. |
| 6,093,550 A | 7/2000 | Chang et al. |
| 6,165,464 A | 12/2000 | Hudziak et al. |
| 6,299,863 B1 | 10/2001 | Aberg et al. |
| 6,365,157 B2 | 4/2002 | Rockwell et al. |
| 6,462,173 B1* | 10/2002 | Lu et al. .............. 530/328 |
| 6,495,376 B1 | 12/2002 | Lu et al. |
| 6,555,583 B2 | 4/2003 | Nieman et al. |
| 6,562,363 B1 | 5/2003 | Mantelle et al. |
| 6,569,839 B1 | 5/2003 | McKay |
| 6,596,848 B1 | 7/2003 | Hunter et al. |
| 6,696,248 B1 | 2/2004 | Knappik et al. |
| 6,706,484 B1 | 3/2004 | Knappik et al. |
| 6,828,422 B1 | 12/2004 | Achim et al. |
| 6,830,745 B1 | 12/2004 | Budny et al. |
| 6,864,275 B1 | 3/2005 | Camden et al. |
| 6,869,974 B1 | 3/2005 | Del Soldato |
| 6,894,033 B2 | 5/2005 | Cruz et al. |
| 6,984,654 B2 | 1/2006 | Camden |
| 7,056,917 B2 | 6/2006 | Nakayama et al. |
| 7,087,648 B1 | 8/2006 | McGrath |
| 7,112,578 B2 | 9/2006 | Levin |
| 7,125,677 B2 | 10/2006 | Hunter et al. |
| 7,125,842 B2 | 10/2006 | Kawabe et al. |
| 7,125,955 B2 | 10/2006 | Hunter et al. |
| 7,148,003 B2 | 12/2006 | Hunter et al. |
| 7,161,060 B1 | 1/2007 | Duff et al. |
| 7,164,012 B1 | 1/2007 | Hunter et al. |
| 7,199,119 B2 | 4/2007 | Burkitt et al. |
| 7,202,259 B2 | 4/2007 | Chen |
| 7,217,737 B2 | 5/2007 | Chen et al. |
| 7,264,963 B1 | 9/2007 | Knappik et al. |
| 8,129,131 B2 | 3/2012 | Lu et al. |
| 8,258,099 B2 | 9/2012 | Lu et al. |
| 2002/0025521 A1 | 2/2002 | Lu et al. |
| 2002/0168684 A1* | 11/2002 | Comb et al. .............. 435/7.1 |
| 2004/0171019 A1 | 9/2004 | Matthews et al. |
| 2005/0221391 A1 | 10/2005 | Davies |
| 2005/0239095 A1 | 10/2005 | Lu et al. |
| 2006/0074222 A1 | 4/2006 | Lu et al. |
| 2006/0258564 A1* | 11/2006 | Pluschke et al. .............. 514/7 |
| 2007/0172496 A1 | 7/2007 | Olesen |
| 2008/0058276 A1 | 3/2008 | Lu et al. |
| 2008/0118505 A1 | 5/2008 | Tedder |
| 2008/0131438 A1 | 6/2008 | Barden et al. |
| 2008/0214470 A1 | 9/2008 | Lu et al. |
| 2008/0248043 A1 | 10/2008 | Babcook et al. |
| 2009/0258352 A1 | 10/2009 | Lu et al. |
| 2010/0278832 A1 | 11/2010 | Kamogawa et al. |
| 2011/0104756 A1 | 5/2011 | Rodriguez et al. |
| 2012/0183560 A1 | 7/2012 | Akassoglou |
| 2013/0028900 A1 | 1/2013 | Lu et al. |
| 2014/0086909 A1 | 3/2014 | Lu et al. |
| 2014/0242100 A1 | 8/2014 | Lu et al. |

FOREIGN PATENT DOCUMENTS

| | | |
|---|---|---|
| WO | WO-96/40072 A2 | 12/1996 |
| WO | WO-97/03692 A1 | 2/1997 |
| WO | WO-97/17986 A1 | 5/1997 |
| WO | WO-99/09969 A1 | 3/1999 |
| WO | WO-02/065091 A2 | 8/2002 |
| WO | WO-02/092765 A2 | 11/2002 |
| WO | WO-2004/016751 A2 | 2/2004 |
| WO | WO-2004/101745 A2 | 11/2004 |
| WO | WO-2005/027727 A2 | 3/2005 |
| WO | WO-2008/006087 A2 | 1/2008 |
| WO | WO-2009/146218 A2 | 12/2009 |
| WO | WO-2011/056561 A1 | 5/2011 |
| WO | WO-2012/162698 A1 | 11/2012 |
| WO | WO-2013/185055 A1 | 12/2013 |
| WO | WO-2014/152157 A2 | 9/2014 |

OTHER PUBLICATIONS

U.S. Appl. No. 61/968,862, Lu et al.
Asuni et al., "Immunotherapy targeting pathological tau conformers in a tangle mouse model reduces brain pathology with associated functional improvements," J Neurosci. 27(34):9115-29 (2007).
Bayry et al., "Intravenous immunoglobulin for infectious diseases: back to the pre-antibiotic and passive prophylaxis era?," Trends Pharmacol Sci. 25(6):306-10 (2004).
Boimel et al., "Efficacy and safety of immunization with phosphorylated tau against neurofibrillary tangles in mice," Exp Neurol. 224(2):472-85 (2010).
Boutajangout et al., "Immunotherapy targeting pathological tau prevents cognitive decline in a new tangle mouse model," J Neurosci. 30(49):16559-66 (2010).
Campbell, General properties and applications of monoclonal antibodies. *Monoclonal Antibody Technology: The Production and Characterization of Rodent and Human Hybridomas.* Elsevier Science, 1-32 (1984).
Casadevall et al., "Passive antibody therapy for infectious diseases," Nat Rev Microbiol. 2(9):695-703 (2004).
Clackson et al., "Making antibody fragments using phage display libraries," Nature. 352(6336):624-8 (1991).
Dunman et al., "Passive immunization as prophylaxis: when and where will this work?," Curr Opin Pharmacol. 3(5):486-96 (2003).
Enever et al., "Next generation immunotherapeutics—honing the magic bullet," Curr Opin Biotechnol. 20(4):405-11 (2009).
Esnault et al., "Pin1 modulates the type 1 immune response," PLoS One. 2(2):e226 (2007) (9 pages).
Huse et al., "Generation of a large combinatorial library of the immunoglobulin repertoire in phage lambda," Science. 246(4935):1275-81 (1989).
International Search Report and Written Opinion for International Application No. PCT/US14/27017, mailed Oct. 28, 2014 (19 pages).
International Search Report for International Application No. PCT/US10/54077, mailed Feb. 15, 2011 (5 pages).
International Search Report for International Application No. PCT/US12/35473, mailed Dec. 10, 2012 (5 pages).
International Search Report for International Application No. PCT/US2012/039850, mailed Oct. 3, 2012 (3 pages).
Jeong et al., "Novel role of Pin1 induction in type II collagen-mediated rheumatoid arthritis," J Immunol. 183(10):6689-97 (2009).
et al., "A conformation- and phosphorylation-dependent antibody recognizing the paired helical filaments of Alzheimer's disease," J Neurochem. 69(5):2087-95 (1997).
Jones et al., "Replacing the complementarity-determining regions in a human antibody with those from a mouse," Nature. 321(6069):522-5 (1986).
Kayed et al., "Prefilament tau species as potential targets for immunotherapy for Alzheimer disease and related disorders," Curr Opin Immunol. 21(3):359-63 (2009).
Köhler et al., "Continuous cultures of fused cells secreting antibody of predefined specificity," Nature. 256(5517):495-7 (1975).
Köhler et al., "Derivation of specific antibody-producing tissue culture and tumor lines by cell fusion," Eur J Immunol. 6(7): 511-519 (1976).
Lim et al., "Pinning down phosphorylated tau and tauopathies," Biochim Biophys Acta. 1739(2-3):311-322 (2005).
Lu et al., "Pinning down proline-directed phosphorylation signaling," Trends Cell Biol. 12(4):164-72 (2002).

(56) References Cited

OTHER PUBLICATIONS

Lu et al., "Prolyl cis-trans isomerization as a molecular timer," Nat Chem Biol. 3(10):619-629 (2007) (11 pages).
Lu et al., "Targeting carcinogenesis: a role for the prolyl isomerase Pin1?," Mol Carcinog. 45(6):397-402 (2006).
Lu et al., "The prolyl isomerase PIN1: a pivotal new twist in phosphorylation signalling and disease," Nat Rev Mol Cell Biol. 8(11):904-16 (2007).
Lu "Pinning down cell signaling, cancer and Alzheimer's disease," Trends Biochem Sci. 29(4):200-9 (2004).
Lummis et al., "Cis-trans isomerization at a proline opens the pore of a neurotransmitter-gated ion channel," Nature. 438(7065):248-52 (2005).
Ma et al., "Antibody catalysis of peptidyl-prolyl cis-trans isomerization in the folding of RNase T1," Proc Natl Acad Sci USA. 95(13):7251-6 (1998).
Marks et al., "By-passing immunization. Human antibodies from V-gene libraries displayed on phage," J Mol Biol. 222(3):581-97 (1991).
Nakamura, et al. "Proline isomer-specific antibodies reveal the early pathogenic tau conformation in Alzheimer's disease" Cell. 149(1):232-44 (2012).
Pastorino et al., "Phosphorylation of the amyloid precursor protein (APP): is this a mechanism in favor or against Alzherimer's disease," Neurosci Res Commun. 35(3):213-31 (2004).
Presta, "Antibody engineering," Curr Opin Struct Biol. 2:593-596 (1992).
Riechmann et al., "Reshaping human antibodies for therapy," Nature. 332(6162):323-7 (1988).
Ubhi et al., "Recent advances in the development of immunotherapies for tauopathies," Exp Neurol. 230(2):157-61 (2011) (12 pages).
Wang et al., "Serine-cis-proline and serine-trans-proline isosteres: stereoselective synthesis of (Z)- and (E)-alkene mimics by Still-Wittig and Ireland-Claisen rearrangements," J Org Chem. 68(6):2343-9 (2003).
Wisniewski et al., "Vaccination as a therapeutic approach to Alzheimer's disease," Mt Sinai J Med. 77(1):17-31 (2010).
Written Opinion of the International Search Authority for International Application No. PCT/US12/35473, mailed Dec. 10, 2012 (7 pages).
Written Opinion of the International Searching Authority for International Application No. PCT/US2012/039850, mailed Oct. 3, 2012 (5 pages).
Wulf et al., "Phosphorylation-specific prolyl isomerization: is there an underlying theme?," Nat Cell Biol. 7(5):435-41 (2005).
Harlow et al., Immunizations. *Antibodies: a Laboratory Manual.* Cold Spring Harbor Laboratory Press, 76 (1988).
Office Action for U.S. Appl. No. 14/113,991, mailed Sep. 2, 2015 (27 pages).
Wittelsberger et al., "Pseudoprolines: Targeting a cis Conformation in a Mimetic of the gp120 V3 Loop of HIV-1," Angew Chem Int Ed Engl. 39(6):1111-5 (2000).
Citron, "Alzheimer's disease: strategies for disease modification," Nat Rev Drug Discov. 9(5):387-98 (2010).

* cited by examiner

METHODS AND COMPOSITIONS FOR THE GENERATION AND USE OF CONFORMATION-SPECIFIC ANTIBODIES

CROSS-REFERENCE TO RELATED APPLICATIONS

This application is a divisional of U.S. patent application Ser. No. 13/504,700, filed Oct. 11, 2012, which is the National Stage of International Application No. PCT/US2010/054077, filed Oct. 26, 2010, which claims the benefit of U.S. Provisional Patent Application No. 61/255,341, filed Oct. 27, 2009.

STATEMENT AS TO FEDERALLY SPONSORED RESEARCH

This invention was made with government support under grants GM058556, AG017870, and AG022082 awarded by NIH. The government has certain rights in the invention.

BACKGROUND OF THE INVENTION

In general, the invention relates to methods and compositions for the generation and use of conformation-specific antibodies or fragments thereof.

Protein phosphorylation is a key cellular signaling mechanism that induces changes in protein conformation. For example, the phosphorylation of specific serine or threonine residues that immediately precede a proline residue (Ser/Thr-Pro motif) is a central regulatory mechanism in the cell. The unique stereochemistry of the proline residue means that the peptidyl-prolyl bond of the Ser/Thr-Pro motif can adopt two different conformational states (i.e., a cis conformation or a trans conformation). Peptidyl-prolyl cis/trans isomerases (PPIases) specifically catalyze the cis/trans isomerization of Ser/Thr-Pro motifs and, thus, regulate the structure of these proteins between the two distinct conformations.

Pin1 is a PPIase that specifically catalyzes the cis/trans isomerization of certain phosphorylated Ser/Thr-Pro (pSer/Thr-Pro) motifs. The identification of Pin1 as a phosphorylation-specific PPIase led to the understanding of a new signaling mechanism, whereby Pin1 catalytically regulates the conformation of its substrates after their phosphorylation to further control protein function. Indeed, Pin1-catalyzed conformational changes control many protein functions. Moreover, Pin1 is tightly regulated by multiple mechanisms, and the deregulation of Pin1 plays a pivotal role in some human diseases (e.g., cancer, Alzheimer's disease, and asthma). Given the completely different conformation of cis and trans Ser/Thr-Pro motifs (e.g., phosphorylated and non-phosphorylated Ser/Thr-Pro motifs), the generation of conformation-specific antibodies would allow for the diagnosis and treatment of disorders associated with specific protein conformations.

Thus, there exists a need in the art for conformation-specific antibodies that specifically bind to a cis or trans conformation of a Xaa-Pro (e.g., Ser/Thr-Pro or phosphorylated Ser/Thr-Pro) motif of a polypeptide, where Xaa may be any amino acid residue.

SUMMARY OF THE INVENTION

In general, the present invention features methods and compositions for the generation and use of conformation-specific antibodies or fragments thereof.

In a first aspect, the invention features an isolated conformation-specific antibody or fragment thereof that specifically binds to a Xaa-Pro motif of a polypeptide, wherein the peptidyl-prolyl bond of the Xaa-Pro motif is in a cis conformation or a trans conformation and wherein Xaa is any amino acid residue. In one embodiment, the antibody is a monoclonal antibody or a polyclonal antibody.

In a second aspect, the invention features an isolated conformation-specific antibody or fragment thereof that specifically binds to a Xaa-Pro motif of a polypeptide, wherein the peptidyl-prolyl bond of the Xaa-Pro motif is in a cis or trans conformation and Xaa is any amino acid residue, produced by a process that includes: (i) providing an antibody library; (ii) contacting the antibody library with a polypeptide that has a Xaa-Pro motif; (iii) determining binding of an antibody from the antibody library to the Xaa-Pro motif of the polypeptide, wherein the antibody specifically binds to the cis or trans conformation of the Xaa-Pro motif of the polypeptide; and (iv) isolating the antibody, wherein the antibody is a conformation-specific antibody. In one embodiment, the antibody library is a synthetic antibody library.

In a third aspect, the invention features a method of generating a conformation-specific antibody or fragment thereof that specifically binds to a Xaa-Pro motif of a polypeptide, where Xaa is any amino acid residue. The method includes: (i) administering a proline-analog-containing antigenic peptide to a host animal, wherein the antigenic peptide has a Xaa-Pro motif; (ii) isolating antisera containing the antibody or fragment thereof produced in the animal; and (iii) purifying the conformation-specific antibody or fragment thereof from the antisera.

In one embodiment of the first, second, or third aspect, the antibody or fragment thereof binds to the cis conformation of the Xaa-Pro motif of the polypeptide with at least 10- to 100-fold greater affinity than to the trans conformation of the Xaa-Pro motif of the polypeptide. In an alternate embodiment, the antibody or fragment thereof binds to the trans conformation of the Xaa-Pro motif of the polypeptide with at least 10- to 100-fold greater affinity than to the cis conformation of the Xaa-Pro motif of the polypeptide. In another embodiment of the first, second, or third aspect, the polypeptide is a PPIase substrate. The PPIase substrate may be a Pin1 substrate (e.g., NIMA, RAB4, CDC25, WEE1, PLK1, MYT1, CDC27, CENP-F, Incenp, RBP1, NHERF-1, KRMP1, CK2, TopoIIα, DAB2, p54nrb, Sil, EMI1, cyclin D1, Ki67, c-Myc, cyclin E, c-Jun, β-catenin, Cf-2, NF-κB, RAF1, c-Fos, RARα, AIB1/SRC-3, HBx, STAT3, p53, Bcl-2, p'73, BimEL, p66$^{Shc}$, CHE1, tau, amyloid precursor protein (APP), APP fragment, synphilin-1, gephyrin, MCL1, NFAT, AUF1, IRF3, BTK, SIN3-RPD3, or hSpt5).

In a fourth aspect, the invention features a method of purifying a conformation-specific antibody or fragment thereof that specifically binds to a Xaa-Pro motif of a polypeptide, wherein the peptidyl-prolyl bond of the Xaa-Pro motif is in a cis conformation and wherein Xaa is any amino acid residue. The method includes: (i) adsorbing a proline-analog-containing antigenic peptide to a support (e.g., a chromatographic support), wherein the antigenic peptide has a Xaa-Pro motif and wherein the peptidyl-prolyl bond of the Xaa-Pro motif of the antigenic peptide is in a cis conformation; (ii) contacting the antigenic peptide on the support with antisera containing the antibody or fragment thereof produced in a host animal, wherein the contacting is under conditions allowing the conformation-specific antibody or fragment thereof to specifically bind to the antigenic peptide; and (iii) eluting the conformation-specific antibody from the antigenic peptide adsorbed to the support.

In one embodiment of the third or fourth aspect, the proline analog is homoproline, pipecolic acid (PIP), dimethyl proline (DMP), azetidine-2-carboxylic acid (Aze), tert-butyl-L-proline (TBP), trans-4-fluoro-L-proline (t-4F-Pro), or cis-4-fluoro-L-proline (c-4F-Pro). In another embodiment, the peptidyl-prolyl bond of the Xaa-Pro motif of the antigenic peptide is fixed in the cis conformation or the trans conformation. In a further embodiment, the antigenic peptide is at least 8 amino acid residues in length (e.g., between 8 and 20 amino acid residues in length). In another embodiment, the conformation-specific antibody is a monoclonal antibody or a polyclonal antibody. In a further embodiment, the host animal is a rabbit.

In a fifth aspect, the invention features a method of diagnosing a subject with a disorder, wherein the disorder is associated with a deregulation of PPIase activity. The method includes: (i) contacting a sample from the subject with a conformation-specific antibody or fragment thereof that specifically binds to a Xaa-Pro motif of a polypeptide present in the sample, wherein the peptidyl-prolyl bond of the Xaa-Pro motif is in a cis conformation and wherein Xaa is any amino acid residue; (ii) quantitating the amount of conformation-specific antibody or fragment thereof bound to the Xaa-Pro motif in the cis conformation; and (iii) comparing the amount of Xaa-Pro motif in the cis conformation in the sample to the amount of Xaa-Pro motif in the cis conformation found in subjects diagnosed with the disorder or subjects not diagnosed with the disorder, wherein an increase in the amount of Xaa-Pro motif in the cis conformation in the subject, in comparison to the amount of Xaa-Pro motif in the cis conformation in subjects not diagnosed with the disorder, indicates that the subject may be diagnosed with the disorder.

In a sixth aspect, the invention features a method of diagnosing a subject with a disorder, wherein the disorder is associated with a deregulation of PPIase activity. The method includes: (i) contacting a sample from the subject with a conformation-specific antibody or fragment thereof that specifically binds to a Xaa-Pro motif of a polypeptide present in the sample, wherein the peptidyl-prolyl bond of the Xaa-Pro motif is in a trans conformation and wherein Xaa is any amino acid residue; (ii) quantitating the amount of conformation-specific antibody or fragment thereof bound to the Xaa-Pro motif in the trans conformation; and (iii) comparing the amount of Xaa-Pro motif in the trans conformation in the sample to the amount of Xaa-Pro motif in the trans conformation found in subjects diagnosed with the disorder or subjects not diagnosed with the disorder, wherein an increase in the amount of Xaa-Pro motif in the trans conformation in the subject, in comparison to the amount of Xaa-Pro motif in the trans conformation in subjects not diagnosed with the disorder, indicates that the subject may be diagnosed with the disorder.

In a seventh aspect, the invention features a method of treating a subject with a disorder, wherein the disorder is associated with a deregulation of PPIase activity. The method includes administering to the subject a pharmaceutical composition that includes a conformation-specific antibody or fragment thereof that specifically binds to a Xaa-Pro motif of a polypeptide present in the subject, wherein Xaa is any amino acid residue and wherein the conformation-specific antibody is present in amount sufficient to treat the disorder. In another embodiment, the method may further include administering an additional therapeutic agent (e.g., a chemotherapeutic agent).

In one embodiment of the fifth, sixth, or seventh aspect, the PPIase is Pin1. In another embodiment, the disorder is a cell proliferation disorder (e.g., cancer), a neurological disorder (e.g., Alzheimer's disease), asthma, a microbial infection, or aging or an aging-related disorder.

In an eighth aspect, the invention features an antigenic peptide with a Xaa-Pro motif that specifically binds to an antibody or fragment thereof, wherein Xaa is any amino acid residue and wherein the antibody or fragment thereof binds to the cis conformation of the Xaa-Pro motif of the antigenic peptide with at least 10- to 100-fold greater affinity than to the trans conformation of the Xaa-Pro motif of the polypeptide.

In a ninth aspect, the invention features an antigenic peptide with a Xaa-Pro motif that specifically binds to an antibody or fragment thereof, wherein Xaa is any amino acid residue and wherein the antibody or fragment thereof binds to the trans conformation of the Xaa-Pro motif of the antigenic peptide with at least 10- to 100-fold greater affinity than to the cis conformation of the Xaa-Pro motif of the polypeptide.

In one embodiment of the eighth or ninth aspect, the proline of the Xaa-Pro motif is a proline analog (e.g., homoproline, pipecolic acid (PIP), dimethyl proline (DMP), azetidine-2-carboxylic acid (Aze), tert-butyl-L-proline (TBP), trans-4-fluoro-L-proline (t-4F-Pro), or cis-4-fluoro-L-proline (c-4F-Pro)). In another embodiment, the peptidyl-prolyl bond of the Xaa-Pro motif of the antigenic peptide is fixed in the cis conformation or the trans conformation. In a further embodiment, the antigenic peptide is at least 8 amino acid residues in length (e.g., between 8 and 20 amino acid residues in length). In one embodiment, the antigenic peptide includes a Xaa-Pro motif of a Pin1 substrate (e.g., a Pin1 substrate listed in Table 1). In an alternate embodiment, the antigenic peptide includes a Xaa-Pro motif of a polypeptide selected from steroid receptors, c-Myb, H3P30, H3P38, Itk, 5-hydroxytryptamine type 3 (5-HT3) receptors, the phage tip protein G3P, the Gag polyprotein of the human immunodeficiency virus-1 (HIV-1) virion, intracellular calcium release channel, CrkII/CrkL proteins, centrosome protein 55 kDa (Cep55), the retroviral Rel proteins, PKB/Akt, human T-cell leukemia virus type 1 (HTLV-1) Tax oncoprotein, Stat3, HER2/Neu, Notch, FAK, FOXO, PML, C/EBP, and SMRT.

In a tenth aspect, the invention features a vaccine composition to induce passive immunity against a disorder associated with a deregulation of PPIase activity (e.g., Alzheimer's disease), wherein the vaccine includes an isolated antibody of the first and/or second aspects and, optionally, an adjuvant. In one embodiment of the tenth aspect, the isolated antibody specifically binds to a Xaa-Pro motif of tau polypeptide (e.g., the cis-pThr231-Pro motif). In another embodiment, the isolated antibody specifically binds to a Xaa-Pro motif of amyloid precursor protein (APP) polypeptide (e.g., the cis-pThr668-Pro motif).

In a final aspect, the invention features a method for providing passive immunity in a subject against a disorder associated with a deregulation of PPIase activity by administering to the subject an effective amount of a vaccine composition of the tenth aspect.

In one embodiment of any of the above aspects, Xaa is a serine or threonine amino acid residue. In another embodiment, Xaa is phosphorylated. In an alternative embodiment, Xaa is not phosphorylated.

As used herein, the term "abnormal cell growth" is intended to include cell growth that is undesirable or inappropriate. Abnormal cell growth also includes proliferation that is undesirable or inappropriate (e.g., unregulated cell proliferation or undesirably rapid cell proliferation). Abnormal cell growth can be benign and result in benign masses of tissue or cells (e.g., benign tumors). Many art-recognized conditions are associated with such benign masses or benign tumors, including, for example, diabetic retinopathy, retrolental fibrioplasia, neovascular glaucoma, psoriasis, angiofibromas, rheumatoid arthritis, hemangiomas, and Karposi's sarcoma. Abnormal cell growth can also be malignant and result in malignancies, malignant masses of tissue or cells, or malignant tumors. Many art-recognized conditions and disorders are associated with malignancies, malignant masses, and malignant tumors, including, for example, cancer and carcinoma.

By "adjuvant" is meant one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include, but are not limited to, aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

By "antibody" is meant monoclonal antibodies, polyclonal antibodies, humanized antibodies, chimeric antibodies, recombinant antibodies, multispecific antibodies, and antibody fragments. The antibody may be, for example, a conformation-specific antibody (e.g., an antibody that binds to the cis or trans conformation of a Xaa-Pro motif). An antibody specifically binds to an antigen. The antibody may also be a non-immunoglobulin binding polypeptide.

By "antigen" is meant a molecule to which an antibody can selectively bind. The target antigen may be a protein (e.g., an antigenic peptide), carbohydrate, nucleic acid, lipid, hapten, or other naturally occurring or synthetic compound. The target antigen may be a polypeptide (e.g., a polypeptide containing a Xaa-Pro motif (e.g., a phosphorylated or non-phosphorylated Ser/Thr-Pro motif)) or peptide mimics (e.g., a polypeptide containing a Xaa-homoproline motif (e.g., a phosphorylated or nonphosphorylated Ser/Thr-homoproline motif)). An antigen may also be administered to an animal to generate an immune response in the animal.

By "binding affinity" is meant the strength of the total noncovalent interactions between a single binding site of a molecule (e.g., an antibody) and its binding partner (e.g., an antigen or antigenic peptide). Unless otherwise indicated, as used herein, "binding affinity" refers to intrinsic binding affinity, which reflects a specific interaction between members of a binding pair (e.g., antibody and antigen). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

By "biological sample" or "sample" is meant solid and fluid samples. Biological samples may include cells, protein or membrane extracts of cells, blood or biological fluids including, e.g., ascites fluid or brain fluid (e.g., cerebrospinal fluid (CSF)). Examples of solid biological samples include samples taken from feces, the rectum, central nervous system, bone, breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, and the thymus. Examples of biological fluid samples include samples taken from the blood, serum, CSF, semen, prostate fluid, seminal fluid, urine, saliva, sputum, mucus, bone marrow, lymph, and tears. Samples may be obtained by standard methods including, e.g., venous puncture and surgical biopsy. In certain embodiments, the biological sample is a breast, lung, colon, or prostate tissue sample obtained by needle biopsy.

By "cancer" and "cancerous" is meant the physiological condition in mammals that is typically characterized by abnormal cell growth. Included in this definition are benign and malignant cancers, as well as dormant tumors or micrometastases. Examples of cancer include, but are not limited to, carcinoma, lymphoma, blastoma, sarcoma, and leukemia. More particular examples of such cancers include, e.g., prostate cancer, squamous cell cancer, small-cell lung cancer, non-small-cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, vulval cancer, thyroid cancer, hepatic carcinoma, gastric cancer, melanoma, and various types of head and neck cancer.

By "cell proliferation disorder" is meant a disorder associated with abnormal cell growth. Exemplary cell proliferative disorders include cancer (e.g., benign and malignant), benign prostatic hyperplasia, psoriasis, abnormal keratinization, lymphoproliferative disorders, rheumatoid arthritis, arteriosclerosis, restenosis, diabetic retinopathy, retrolental fibrioplasia, neovascular glaucoma, angiofibromas, hemangiomas, Karposi's sarcoma, and neurodegenerative disorders. Cellular proliferative disorders are described, for example, in U.S. Pat. Nos. 5,639,600, 7,087,648, and 7,217,737, hereby incorporated by reference.

By "conformation-specific antibody" is an antibody or fragment thereof that recognizes and specifically binds to a particular conformation (e.g., a conformational isomer or conformer) of its complementary antigen. For example, as described herein, the conformation-specific antibody may specifically bind to the cis conformation of a Xaa-Pro motif, but will not specifically bind to the trans conformation of the Xaa-Pro motif, where Xaa is any amino acid residue (e.g., serine or threonine). In this case, the conformation-specific antibody will have, for example, at least 10- to 100-fold greater affinity to the cis conformation than to the trans conformation of a Xaa-Pro motif. Conversely, the conformation-specific antibody may specifically bind to the trans conformation of a Xaa-Pro motif, but will not specifically bind to the cis conformation of the Xaa-Pro motif, where Xaa is any amino acid residue (e.g., serine or threonine). In certain embodiments, the Ser/Thr-Pro motif may be phosphorylated (i.e., pSer/Thr-Pro).

By "disorder" is meant any condition that may be treated, inhibited, diagnosed, or screened for according to the methods of the invention described herein. By "disorder associated with a deregulation of PPIase activity" is meant a disorder in which PPIase (e.g., Pin1) activity is modulated (e.g., upregulated or downregulated). Non-limiting examples of disorders associated with a deregulation of PPIase activity to be treated, inhibited, diagnosed, or screened for by the methods and compositions described herein include, e.g., cellular proliferation disorders (e.g., cancer), neurological disorders (e.g., Alzheimer's disease), aging-related disorders, asthma, and microbial infections.

By "fragment" is meant a portion of a nucleic acid or polypeptide (e.g., an antibody) that contains at least, e.g., 10%, 20%, 30%, 40%, 50%, 60%, 70%, 80%, 90%, 95%, or more of the entire length of the nucleic acid or polypeptide. A nucleic acid fragment may contain, e.g., 10, 20, 30, 40, 50, 60, 70, 80, 90, or 100, 200, 300, 400, 500, 600, 700, 800, 900, 1000, 1100, 1200, 1300, 1400, 1500, 2000, 2500, 3000, 4000, 4500, or 5000 nucleotides or more nucleotides, up to the full length of the nucleic acid. A polypeptide fragment may contain, e.g., 10, 20, 30, 40, 50, 60, 70, 80, 90, 100, 150, 200, 250, 300, 350, 400, 450, or 500 amino acids or more amino acids, up to the full length of the polypeptide. Fragments useful in the therapeutic methods of the invention include, e.g., fragments of conformation-specific antibodies that retain biological activity (e.g., fragments that bind to a specific conformational state). Fragments can be modified as described herein and as known in the art.

By "humanized antibody" is meant an immunoglobulin amino acid sequence variant or fragment thereof that is capable of binding to a predetermined antigen. The antibody may contain both the light chain, as well as at least the variable domain of a heavy chain. The antibody also may include the CH1, hinge, CH2, CH3, or CH4 regions of the heavy chain. The humanized antibody comprises a framework region (FR) having substantially the amino acid sequence of a human immunoglobulin and a complementarity determining region (CDR) having substantially the amino acid sequence of a non-human immunoglobulin.

Generally, a humanized antibody has one or more amino acid residues introduced into it from a source that is non-human. In general, the humanized antibody may comprise substantially all of at least one, and typically two, variable domains (e.g., Fab, Fab', F(ab')$_2$, Fabc, or Fv) in which all or substantially all of the CDR regions correspond to those of a non-human immunoglobulin and all or substantially all of the FR regions are those of a human immunoglobulin consensus sequence. The humanized antibody may comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region" is meant the sequences of amino acids located on either side of the three hypervariable sequences of the immunoglobulin light and heavy chains. See, e.g., Jones et al., *Nature* 321:522-525 (1986); Riechmann et al., *Nature* 332:323-329 (1988); and Presta, *Curr. Op. Struct. Biol.* 2:593-596 (1992), and U.S. Pat. Nos. 4,816,567 and 5,530,101, hereby incorporated by reference.

The term "monoclonal antibody," as used herein, refers to an antibody obtained from a population of substantially homogeneous antibodies (i.e., the individual antibodies comprising the population are identical except for possible naturally occurring mutations that may be present in minor amounts). Monoclonal antibodies are highly specific, being directed against a single antigenic site. Furthermore, in contrast to conventional (e.g., polyclonal) antibody preparations, which typically include different antibodies directed against different determinants (e.g., epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by Kohler et al. (see, e.g., Nature 256: 495, 1975) or may be made by recombinant DNA methods (see, e.g., U.S. Pat. No. 4,816,567). Monoclonal antibodies may also be isolated from phage antibody libraries using the techniques described in Clackson et al. (Nature 352: 624-628, 1991) and Marks et al. (J. Mol. Biol. 222: 581-597, 1991), for example.

By "neurological disorder" is meant a disturbance in the structure or function of the nervous system resulting from a developmental abnormality, disorder, injury, or toxin. Exemplary neurological disorders include Alzheimer's disease (AD), mild cognitive impairment (MCI), Parkinson's disease (PD), multiple sclerosis (MS), muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalistis, convulsive disorders (e.g., epilepsy), vascular dementia, age-related dementia, head trauma, stroke, neurofibromatosis, Lewy body disease, amyotrophic lateral sclerosis (ALS), peripheral neuropathies, and macular degeneration.

By "passive immunity" is meant temporary immunity to a specific infection, disease, or disorder induced in a subject by providing to the subject externally produced immune molecules (e.g., antibodies or immunoglobulins).

By "pharmaceutically acceptable carrier" is meant a carrier that is physiologically acceptable to the treated subject while retaining the therapeutic properties of the composition (e.g., the conformation-specific antibody) with which it is administered. One exemplary pharmaceutically acceptable carrier substance is physiological saline. Other physiologically acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, Pa.).

By "protein," "polypeptide," "polypeptide fragment," or "peptide" is meant any chain of more than two amino acid residues, regardless of post-translational modification (e.g., glycosylation or phosphorylation), constituting all or part of a naturally occurring polypeptide or peptide or constituting a non-naturally occurring polypeptide or peptide. A polypeptide or peptide may be said to be "isolated" or "substantially pure" when physical, mechanical, or chemical methods have been employed to remove the polypeptide from cellular constituents. An "isolated polypeptide" (e.g., an isolated antibody), "substantially pure polypeptide," or "substantially pure and isolated polypeptide" is typically considered removed from cellular constituents and substantially pure when it is at least 60% by weight free from the proteins and naturally occurring organic molecules with which it is naturally associated. The polypeptide may be at least 75%, 80%, 85%, 90%, 95%, or 99% by weight pure. A substantially pure polypeptide (e.g., a substantially pure antibody or fragment thereof) may be obtained by standard techniques, for example, by extraction from a natural source (e.g., cell lines or biological fluids), by expression of a recombinant nucleic acid encoding the polypeptide, or by chemically synthesizing the polypeptide. Purity can be measured by any appropriate method, e.g., by column chromatography, polyacrylamide gel electrophoresis, or HPLC analysis. Alternatively, a polypeptide is considered isolated if it has been altered by human intervention, placed in a location that is not its natural site, or if it is introduced into one or more cells.

The peptides and polypeptides of the invention, as defined above, include all "mimetic" and "peptidomimetic" forms. The terms "mimetic" and "peptidomimetic" refer to a synthetic chemical compound that has substantially the same structural and/or functional characteristics of the peptides (e.g., antigenic peptides) or polypeptides of the invention. The mimetic can be either entirely composed of synthetic, non-natural analogs of amino acids or may be a chimeric molecule of natural amino acids and non-natural analogs of amino acids. The mimetic can also incorporate any amount of conservative substitutions, as long as such substitutions do not substantially alter the mimetic's structure or activity.

By "proline analog" is meant a molecule substantially similar in function to either an entire proline amino acid residue or to a fragment thereof. For example, the present invention contemplates the use of proline analogs wherein a side chain is lengthened or shortened while still providing a carboxyl, amino, or other reactive precursor functional group, as well as proline analogs having variant side chains with appropriate functional groups. Exemplary proline analogs include, without limitation, homoproline (i.e., pipecolic acid (PIP)), dimethyl proline (DMP), azetidine-2-carboxylic acid (Aze), tert-butyl-L-proline (TBP), trans-4-fluoro-L-proline (t-4F-Pro), or cis-4-fluoro-L-proline (c-4F-Pro).

By "reduce or inhibit" is meant the ability to cause an overall decrease of 20% or greater, of 50% or greater, or of 75%, 80%, 85%, 90%, 95%, or greater. For therapeutic applications, to "reduce or inhibit" can refer to the symptoms of the disorder being treated or the presence or extent of a disorder being treated. For diagnostic or monitoring applications, to "reduce or inhibit" can refer to a decrease in the level of protein or nucleic acid detected by the diagnostic or monitoring assays.

By "reference" is meant any sample, standard, or level that is used for comparison purposes. A "normal reference sample" can be a prior sample taken from the same subject prior to the onset of a disorder (e.g., a cellular proliferation disorder or a neurological disorder), a sample from a subject not having the disorder, a subject that has been successfully treated for the disorder, or a sample of a purified reference polypeptide at a known normal concentration. By "reference standard or level" is meant a value or number derived from a reference sample. A normal reference standard or level can be a value or number derived from a normal subject that is matched to a sample of a subject by at least one of the following criteria: age, weight, disease stage, and overall health. In one example, a normal reference level of, for example, a polypeptide indicative of a disorder or a conformation of a polypeptide indicative of a disorder, is less than 5 ng/ml in a serum sample, less than 4 ng/ml, less than 3 ng/ml, less than 2 ng/ml, or less than 1 ng/ml in a serum sample. A "positive reference" sample, standard, or value is a sample, standard, value, or number derived from a subject that is known to have a disorder (e.g., a cellular proliferation disorder or a neurological disorder) that is matched to a sample of a subject by at least one of the following criteria: age, weight, disease stage, and overall health. For example, a positive reference value for, e.g., a polypeptide indicative of a disorder, is greater than 5 ng/ml serum, greater than 10 ng/ml serum, greater than 20 ng/ml, greater than 30 ng/ml, greater than 40 ng/ml, or greater than 50 ng/ml serum.

By "specifically binds" is meant a molecule (e.g., an antibody) which recognizes and binds another molecule (e.g., an antigen), but that does not substantially recognize and bind other molecules. In one example, an antibody that specifically binds the cis conformation of a Xaa-Pro motif of a polypeptide does not specifically bind the trans conformation of a Xaa-Pro motif of a polypeptide, where Xaa is any amino acid residue (e.g., serine or threonine) The term "specific binding," "specifically binds to," or is "specific for" a particular molecule (e.g., a polypeptide, an epitope on of a polypeptide, or a conformation of a polypeptide), as used herein, can be exhibited, for example, by a molecule having a $K_d$ for the molecule to which it binds of at least about $10^{-4}$M, $10^{-5}$M, $10^{-6}$M, $10^{-7}$M, $10^{-8}$M, $10^{-9}$M, $10^{-10}$ M, $10^{-11}$ M, $10^{-12}$ M, or greater.

The term "specifically binds" may also refer to binding where a molecule (e.g., an antibody) binds to a particular polypeptide (e.g., a polypeptide containing a Xaa-Pro motif, where Xaa is any amino acid residue (e.g., serine or threonine)), an epitope on a particular polypeptide, or a conformation of a particular polypeptide (e.g., a cis conformation of a Xaa-Pro motif) without substantially binding to any other polypeptide, polypeptide epitope, or polypeptide conformation (e.g., the trans conformation of a Xaa-Pro motif). For example, the conformation-specific antibody may have, for example, at least 10- to 100-fold greater affinity (e.g., $10^1$-, $10^2$-, $10^3$-, $10^4$-, $10^5$-, $10^6$-, $10^7$-, $10^8$-, $10^9$-, or $10^{10}$-fold greater affinity) to one conformation (e.g., the cis conformation) than to another conformation (e.g., the trans conformation) of, for example, a Ser/Thr-Pro motif. By "subject" is meant a mammal, including, but not limited to, a human or non-human mammal, such as a bovine, equine, canine, ovine, or feline.

By "therapeutic amount" is meant an amount that, when administered to a subject suffering from a disorder (e.g., a cellular proliferative disorder, a neurological disorder, asthma, or a microbial infection), is sufficient to cause a qualitative or quantitative reduction in the symptoms associated with the disorder.

By "treating" is meant administering a pharmaceutical composition for therapeutic purposes or administering treatment to a subject already suffering from a disorder to improve the subject's condition. By "treating a disorder" is meant that the disorder and the symptoms associated with the disorder are, e.g., alleviated, reduced, cured, or placed in a state of remission.

By "vaccine," as used herein, is meant a composition that elicits an immune response in a subject to which it is administered.

Other features and advantages of the invention will be apparent from the following detailed description, the drawings, and the claims.

BRIEF DESCRIPTION OF THE DRAWINGS

FIGS. 5A and 5B are micrographs showing human brain samples immunostained with cis- or trans-pT231-tau antibodies. FIGS. 5C and 5D are micrographs showing human brain samples immunostained with cis-pT231-tau antibodies and TG3 monoclonal antibody. TG3 antibody recognizes pT231-tau in the conformation that is only detected in AD brains, but not in normal human brains or MCI brains.

FIG. 6C is a bar graph showing the cis/trans ratio ("nd": not detectable; "na": not applicable).

DETAILED DESCRIPTION

We describe the generation, purification, and use of conformation-specific antibodies. In particular, we have generated and purified antibodies specific to the cis or trans conformation of the phosphorylated Ser/Thr-Pro motif using antigenic formulations containing proline analogs. The same strategy can be used to generate and purify antibodies specific to the cis or trans conformation of a Xaa-Pro motif, where Xaa is any amino acid residue. Such conformation-specific antibodies may be useful for the treatment, diagnosis, and monitoring of certain disorders, including, e.g., cancer, Alzheimer's disease, asthma, inflammation, immune diseases, and aging.

PPIases and the Cis/Trans Conformation of PPIase Substrates

Figure 1:
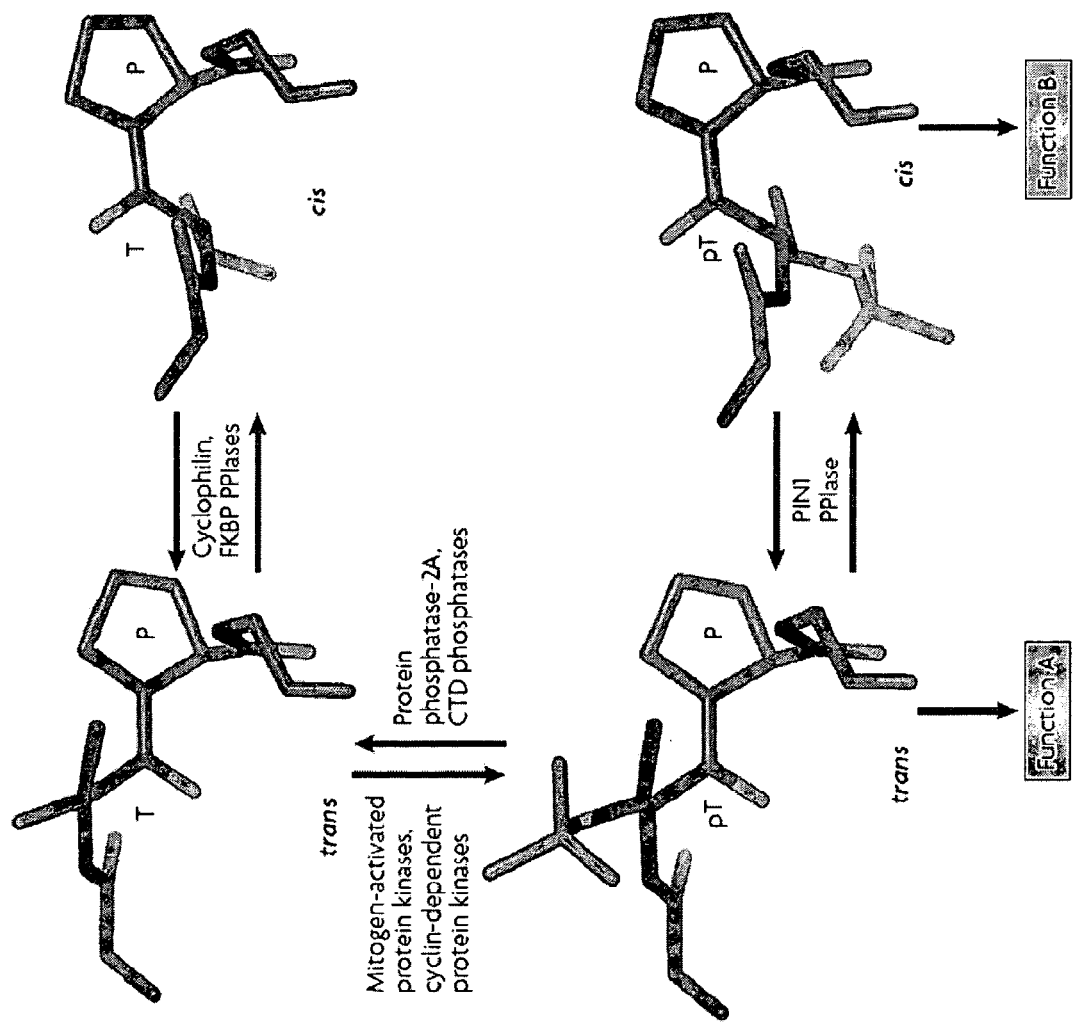
FIG. 1 is a schematic diagram showing the Pin1-catalyzed conformational switch between the cis and trans conformation of pSer/Thr-Pro motifs.
Figure 2:
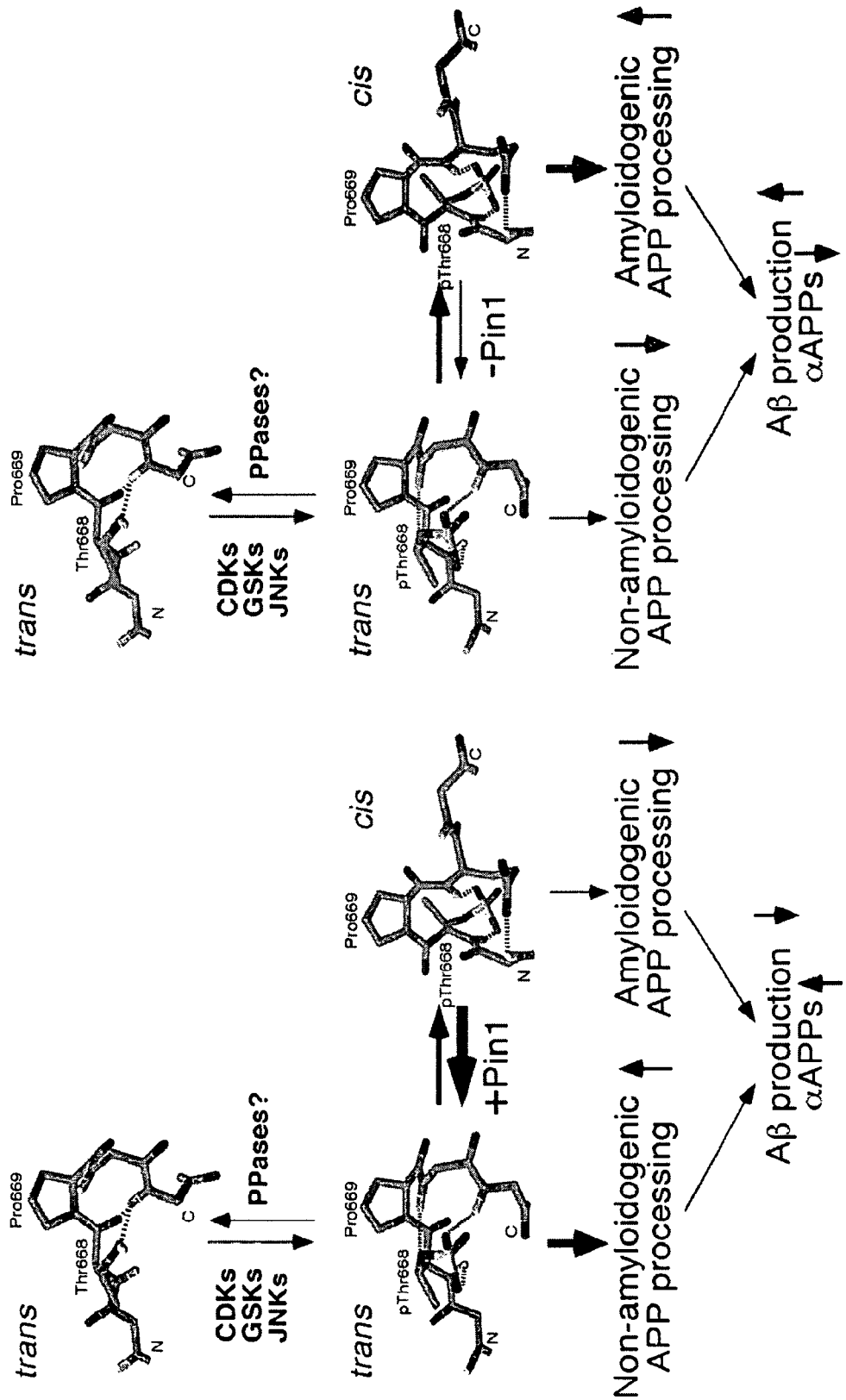
FIG. 2 is a schematic diagram showing that phosphorylation-dependent prolyl cis-trans isomerization acts as a molecular timer in amyloid precursor protein (APP) processing and Aβ production in Alzheimer's disease (AD). Phosphorylation of APP on the Thr668-Pro motif occurs during mitosis in the cell cycle and is also increased in AD brains. Before phosphorylation, the Thr668-Pro motif in APP is in a trans conformation in a helix cap structure. Although the pThr668-Pro motif of APP is likely phosphorylated in trans by upstream kinases, it has a tendency to be in cis, with the overall content being ~10% due to both destabilization of the trans isomer by loss of hydrogen bonds resulting from a local unfolding of a helix cap and to stabilization of the cis isomer by hydrogen bonds involving the phosphate. Pin1 accelerates both $k_{cis\ to\ trans}^{cat}$ and $k_{trans\ to\ cis}^{cat}$ by several orders of magnitude over the typical uncatalyzed isomerization rates for pThr-Pro peptides, resulting in a dramatic reduction in the average lifetime of both the cis (~0.05 s) and trans (~0.5 s) isomeric states to fractions of a second, with the catalyzed cis to trans rate being 10-fold faster than the catalyzed trans to cis rate. This favors more non-amyloidogenic APP processing, reducing Aβ production (FIG. 2A). In contrast, without proper Pin1 function, the cis pThr668-Pro motif may not be isomerized to trans, which might favor more amyloidogenic APP processing and Aβ production (FIG. 2B). Therefore, in collaboration with other AD factors, Pin1 deregulation can promote non-amyloidogenic APP processing and Aβ production.

Proline is an amino acid residue unique in its ability to adopt either the cis or trans conformation. Due to the relatively large energy barrier of its isomerization ($\epsilon^u$=14 to 24 kcal mol$^{-1}$), uncatalyzed isomerization is a slow process, but may be accelerated by PPIases (see, e.g., FIGS. 1 and 2). PPIases facilitate protein folding and include, for example, cyclophilins (Cyps), FK506-binding proteins (FKBPs), and parvulin-like PPIases (e.g., Ess1 and Pin1).

Pin1 (protein interacting with NIMA (never in mitosis A)-1) specifically isomerizes phosphorylated Ser/Thr-Pro (pSer/Thr-Pro) motifs of certain polypeptides, which is important because proline-directed kinases (e.g., protein kinases that phosphorylate certain Ser/Thr residues that precede a proline residue) and phosphatases are conformation-specific and generally act only on the trans conformation. Pin1 has a two-domain structure that includes an N-terminal WW domain and a C-terminal PPIase domain, and structure-function analyses have shown that the unique substrate specificity of Pin1 towards specific pSer/Thr-Pro motifs results from interactions provided by both the WW domain and the PPIase domain. The PPIase activity of Pin1 facilitates the regulation of, for example, growth-signal responses, cell-cycle progression, cellular stress responses, neuronal function, and immune responses.

Exemplary substrates of Pin1, each containing motifs capable of being isomerized, are listed in Table 1. The functional consequences of isomerization of the substrates are also listed.

TABLE 1

| Pin1 Substrates | | |
|---|---|---|
| Substrate (GenBank Accession Number) | Targeting Site(s) | Functional Consequence of PPIase Activity of Pin1 Upon Substrate |
| G2/M and Mitotic Regulation | | |
| NIMA (P11837) | — | Regulation of mitotic function |
| RAB4 (NP_004569) | — | — |
| CDC25 (AAA58417) | pThr48/67-Pro | Dephosphorylation and regulation of activity |
| WEE1 (NP_003381) | pT186-P | Inhibition of WEE1 activity |
| PLK1 (P53350) | — | — |
| MYT1 (NP_004194) | — | — |
| CDC27 (AAH11656) | — | — |
| CENP-F (P49454) | — | — |
| Incenp (NP_064623) | — | — |
| RPB1 (CAA65619) | pSer5-Pro | Regulation of CTD dephosphorylation |
| NHERF-1 (AAA80218) | pSer279/301-P | Dephosphorylation |
| KRMP1 (NP_057279) | pT-1604-P | Regulation of mitotic function |

TABLE 1-continued

Pin1 Substrates

| Substrate (GenBank Accession Number) | Targeting Site(s) | Functional Consequence of PPIase Activity of Pin1 Upon Substrate |
|---|---|---|
| CK2 (NP_808227) | Multiple pSer/Thr-Pro sites | Inhibition of kinase activity |
| TopoIIα (NP_001058) | — | Inhibition or induction of phosphorylation |
| DAB2 (NP_001334) | — | Dephosphorylation |
| p54nrb (CAA72157) | Multiple pSer/Thr-Pro sites | — |
| Sil (CAC14001) | Multiple pSer/Thr-Pro sites | Regulation of function |
| EMI1 (NP_036309) | pS10-P | Stabilization |
| G1/S Regulation | | |
| Cyclin D1 (NP_444284) | pT286-P | Stabilization and nuclear localization |
| Ki67 | pT234-P | — |
| c-Myc (CAA46984) | pT58-P | Dephosphorylation and destabilization |
| Cyclin E (P24864) | pS384-P | Destabilization |
| Growth and Oncogenic Signaling | | |
| c-Jun (AAH06175) | pS63/73-P | Transactivation |
| B-catenin (P35222) | pS246-P | Stabilization, protein interaction, and transactivation |
| Cf-2 (NP_034298) | — | Destabilization |
| NF-κB (AAH33210) | pT254-P | Stabilization, protein interaction, and transactivation |
| RAF1 (AAA60247) | Multiple pSer/Thr-Pro sites | Dephosphorylation and prolonging activation |
| c-Fos (CAA24756) | Multiple pSer/Thr-Pro sites | Transactivation |
| RARα (NP_001019980) | pS77-P | Stabilization and transactivation |
| AIB1/SRC-3 | — | Transactivation and destabilization |
| HBx (NP_110380) | pS41-P | Stabilization and potentiation |
| STAT3 (NP_998827) | pS727-P | Transactivation |
| DNA Damage, Oxidative Stress Response, and Apoptosis | | |
| p53 (BAC16799) | Multiple pSer/Thr-Pro sites | Stabilization and transactivation |
| Bcl-2 (NP_000648) | pS70/87-P | — |
| p73 (CAA72221) | Multiple pSer/Thr-Pro sites | Stabilization and transactivation |
| BimEL (AAC39593) | pS65-P | Stabilization |
| p66$^{shc}$ (AAH14158) | — | Mitochondrial import |
| CHE1 (P06276) | — | Destabilization |
| Neuronal Survival and Degeneration | | |
| Tau (NP_058519) | pT231-P pT212-P | Dephosphorylation and protein interaction |
| APP (P05067) | pT668-P | Promotes non-amyloidogenic APP processing and reduces Aβ production |
| APP fragment | pT668-P | Increases Aβ production from C99 APP fragment |
| Synphilin-1 (AAD30362) | pS211/215-P | Protein interaction |
| Gephyrin (CAC81240) | pS188/194/200-P | Protein interaction |
| MCL1 (CAI15504) | pT163-P | Stabilization |
| Immune Response and Asthma | | |
| NFAT (NP_666017) | — | |
| AUF1 (NP_112738) | — | Protein interaction |
| IRF3 (AAH71721) | pS339-P | Destabilization |
| BTK (CAI42359) | pS21/115-P | Destabilization |
| Others | | |
| SIN2-RPD3 | — | Reduces histone deacetylases |
| hSpt5 (NP_001124297) | — | |

The importance of phosphorylation-independent prolyl isomerization has also been documented. For example, the PPIase CypA catalyzes the cis-trans isomerization of the prolyl bond at position Gly237-Pro238 of the Crk protein. Other PPIase substrates isomerized in a phosphorylation-independent manner include, without limitation, steroid receptors, c-Myb, H3P30, H3P38, Itk, 5-hydroxytryptamine type 3 (5-HT3) receptors, the phage tip protein G3P, the Gag polyprotein of the human immunodeficiency virus-1 (HIV-1) virion, intracellular calcium release channel, CrkII/CrkL proteins, centrosome protein 55 kDa (Cep55), the retroviral Rel proteins, PKB/Akt, human T-cell leukemia virus type 1 (HTLV-1) Tax oncoprotein, Stat3, HER2/Neu, Notch, FAK, FOXO, PML, C/EBP, and SMRT. Deregulation of PPIase activity (e.g., the upregulation or downregulation of PPIase activity (e.g., an increase or decrease in PPIase activity)) may, for example, result in a greater cis or trans content of Ser/Thr-Pro motifs present in PPIase substrates, which may affect the function of the PPIase substrate and result in the development of, e.g., cellular proliferation disorders, neurological disorders, asthma, or aging-associated disorders.

Conformation-Specific Antibodies

The present invention describes methods and compositions for the generation and use of conformation-specific antibodies or fragments thereof. Conformation-specific antibodies may, for example, specifically bind to the cis or trans conformation of a polypeptide. In a specific embodiment, the conformation-specific antibody of the invention may bind to the cis conformation of a phosphorylated or non-phosphorylated Xaa-Pro motif of a polypeptide. The conformation-specific antibody may, alternatively, bind to the trans conformation of a phosphorylated or nonphosphorylated Xaa-Pro motif of a polypeptide. The Xaa-Pro motif may be a phosphorylated Ser/Thr-Pro motif of a polypeptide (e.g., a Pin1 substrate). The binding of a conformation-specific antibody to its antigen (e.g., a Pin1 substrate) may be useful in the treatment, diagnosis, or monitoring of a disorder or the progression of a disorder.

Methods for the preparation and use of antibodies for therapeutic purposes are described herein and, for example, in U.S. Pat. Nos. 6,054,297; 5,821,337; 6,365,157; and 6,165,464, hereby incorporated by reference.

Antigens

Conformation-specific antibodies of the present invention may be generated using immunogenic antigens (e.g., antigenic peptides) containing, for example, a phosphorylated or nonphosphorylated Xaa-Pro motif, where Xaa is any amino acid residue (e.g., serine or threonine) fixed in a particular conformation (e.g., the cis or trans conformation) or in mixed cis and trans conformations or any other motif or amino acid sequence that is capable of cis/trans isomerization. For example, the cis or trans content of phosphorylated or nonphosphorylated Ser/Thr-Pro-containing antigenic peptides of the invention may be fixed by stereoselective synthesis of (Z)- and (E)-alkene mimics by Still-Wittig and Ireland-Claisen rearrangements (J. Org. Chem., 68: 2343-2349, 2003; hereby incorporated by reference). Alternatively, the cis or trans content of phosphorylated or nonphosphorylated Ser/Thr-Pro-containing antigenic peptides of the invention may be increased or fixed by substituting a proline amino acid residue with a proline analog. Proline analogs include, without limitation, homoproline, pipecolic acid (Pip), dimethyl proline (DMP), azetidine-2-carboxylic acid (Aze), tert-butyl-L-proline (TBP), trans-4-fluoro-L-proline (t-4F-Pro), and cis-4-fluoro-L-proline (c-4F-Pro). The cis or trans content of a given antigen may be analyzed by, for example, nuclear magnetic resonance (NMR) analysis.

Antigenic peptides of the invention may contain a phosphorylated or nonphosphorylated Xaa-Pro motif, wherein Xaa is any amino acid residue (e.g., serine or threonine), which is capable of cis/trans isomerization. The antigenic peptide may contain the amino acid residues of the Xaa-Pro motif of a Pin1 substrate (examples of which are provided in Table 1), with the proline residue substituted for a proline analog. The antigenic peptide may also contain the amino acid residues of the Xaa-Pro motif of a full-length polypeptide, wherein the full-length polypeptide is any of the following polypeptides or any isoform thereof: steroid receptors, c-Myb (GenBank Accession No. AAA52032), Itk (GenBank Accession No. BAA02873), 5-hydroxytryptamine type 3 (5-HT3) receptors (GenBank Accession Nos. NP_001157118, NP_570126, and NP_872395), the phage tip protein G3P, the Gag polyprotein of the human immunodeficiency virus-1 (HIV-1) virion (GenBank Accession No. AAD39400), intracellular calcium release channel, CrkII/CrkL proteins (GenBank Accession Nos. NP_058431, NP_005197, CAG30309, and CAA42199), centrosome protein 55 kDa (Cep55) (GenBank Accession Nos. NP_001120654 and NP_060601), the retroviral Rel proteins (GenBank Accession No. NP_002899 and ABC40747), PKB/Akt (GenBank Accession No. NP_001014432 and NP_005154), human T-cell leukemia virus type 1 (HTLV-1) Tax oncoprotein (GenBank Accession No. P03409), Stat3 (GenBank Accession No. AAK17196), HER2/Neu (GenBank Accession No. AAD14920), Notch (GenBank Accession Nos. NP_476859), FAK (GenBank Accession Nos. AAA58469, NP_005598, and NP_722560), FOXO (GenBank Accession No. 016850), PML (GenBank Accession No. AAB19601), C/EBP (GenBank Accession Nos. AAA28415 and AAB33475), and SMRT (GenBank Accession Nos. Q9WU42 and AAC50236). The antigenic peptide may further include additional residues surrounding the Xaa-Pro motif of the full-length polypeptide. For example, the antigenic peptide may include the 3-10 amino acid residues N-terminal to the Xaa residue of a full-length polypeptide and the 3-10 amino acid residues C-terminal to the proline of a full-length polypeptide.

The antigenic peptide of the invention may be, for example, at least 4, 5, 6, 7, or 8 amino acid residues in length. The antigenic peptide may be between 8 and 20 amino acid residues in length (e.g., 8, 9, 10, 11, 12, 13, 14, 15, 16, 17, 18, 19, or 20 amino acids residues in length) or may be over 20 amino acid residues in length.

Such antigens may be produced and purified by any of a variety of methods known to one of skill in the art. Antigenic peptides may be produced and purified by, e.g., solid-phase chemical synthesis, in vitro transcription/translation, or by recombinant technology. The antigenic peptides may optionally be chemically coupled to a carrier protein or the peptides may be generated as fusion proteins to increase antigenicity. Antigenic peptides may be screened based upon their ability to induce the production of conformation-specific antibodies. In this respect, such screening techniques may include, but are not limited to, enzyme-linked immunosorbant assays (ELISA), immunoprecipitation, or other immunoassays.

Exemplary antigens useful in the production of conformation-specific antibodies include antigens containing a phosphorylated or nonphosphorylated Ser/Thr-homoproline, Ser/Thr-Pip, Ser/Thr-DMP, Ser/Thr-Aze, Ser/Thr-TBP, Ser/Thr-t-4F-Pro, Ser/Thr-c-4F-Pro motif. Specific examples of such antigens include, e.g., pThr668-Pip and pThr668-DMP APP peptide (VDAAV-pThr668-Pro-EERHLSK; SEQ ID NO: 1), pThr231-Pip tau peptide, and pThr231-DMP tau peptide (KVAVVR-pThr231-Pro-PKSPS; SEQ ID NO: 2). Other exemplary antigens are also described in U.S. Patent Application Publication No. 2008/0058276, hereby incorporated by reference. Such peptides may be used as antigens for generating, e.g., polyclonal or monoclonal antibodies (e.g., rabbit or mouse monoclonal antibodies).

Generation and Purification of Conformation-Specific Antibodies

The antigens of the present invention may be used to generate, for example, monoclonal, polyclonal, chimeric, humanized, or recombinant conformation-specific antibodies by any method known in the art. These methods include the immunological methods described by Kohler and Milstein (Nature 256: 495-497, 1975 and Eur. J. Immunol. 6: 511-519, 1976) and Campbell ("Monoclonal Antibody Technology, The Production and Characterization of Rodent and Human Hybridomas," in Burdon et al., Eds., Laboratory Techniques in Biochemistry and Molecular Biology, Volume 13, Elsevier Science Publishers, Amsterdam, 1985), as well as by the recombinant DNA method described by Huse et al. (Science 246: 1275-1281, 1989).

Briefly, the antigens of the present invention may, in combination with an adjuvant, be administered to a host animal (e.g., a rabbit, mouse, goat, sheep, or chicken). The administration of such antigens may be accomplished by any of a variety of methods, including, but not limited to, subcutaneous or intramuscular injection. Once administered, the results of antibody titers produced in the host animal are monitored, which may be conducted by any of a variety of techniques well-known in the art (e.g., routine bleeds), with the antisera being isolated (e.g., via centrifugation) and thereafter screened for the presence of antibodies having a binding affinity for, e.g., the cis or trans conformation of a polypeptide or polypeptide fragment. Screening for the desired antibody may be accomplished by techniques including, e.g., radioimmunoassays, ELISA, sandwich immunoassays, immunoradiometric assays, gel diffusion precipitation reactions, in situ immunoassays (e.g., using colloidal gold, enzymatic, or radioisotope labels), Western blots, precipitation reactions, agglutination assays (e.g., gel agglutination assays or hemagglutination assays), complement fixation assays, immunofluorescence assays, protein A assays, and immunoelectrophoresis assays.

The resultant antisera derived from the host animal may be affinity purified to derive the antibodies for the present invention. The antisera may be purified via conventional techniques, such as the introduction of the antisera onto a separation column. The antigens of the present invention may be immobilized on the column to isolate and purify conformation-specific antibodies. For example, an antigenic peptide containing a Ser/Thr-DMP motif that is used to generate a cis-specific antibody may be immobilized on a column and used to purify the resulting cis-specific antibody from, e.g., antibodies in the trans conformation. The column may then be washed to remove antibodies not having specificity for the antigen immobilized on the column, with the remaining conformation-specific antibody ultimately being eluted from the column. The isolated conformation-specific antibody may then be stored per conventional practices known to those skilled in the art.

Alternatively, antibody libraries (e.g., naive antibody libraries, synthetic antibody libraries, semi-synthetic antibody libraries, or combinatorial libraries) may be screened for the identification of conformation-specific antibodies. Such libraries are commercially available from a number of sources (e.g., Cambridge Antibody, Cambridge, United Kingdom, Genetastix Corporation, Pacific Northwest Laboratory, Richland, Wash., and MorphoSys AG, Munich, Germany (e.g., HuCal GOLD)). See, e.g., U.S. Pat. Nos. 6,696,248; 6,706,484; 6,828,422; and 7,264,963, hereby incorporated by reference.

Screening of an antibody library may be performed by using one of the methods known to one of skill in the art including, e.g., phage-display, selectively infective phage, polysome technology, and assay systems for enzymatic activity or protein stability. Antibodies having the desired property can be identified, for example, by sequencing of the corresponding nucleic acid sequence, by amino acid sequencing, or by mass spectrometry. Optimization is performed by replacing sub-sequences with different sequences (e.g., random sequences) and then repeating the screening step one or more times. The antibodies may be screened for, e.g., optimized affinity or specificity for a target molecule (e.g., the cis or trans conformation of a target molecule), optimized expression yields, optimized stability, or optimized solubility.

Conformation-specific antibodies of the present invention recognize and specifically bind to, for example, a particular conformation (e.g., the cis or trans conformation) of its complementary antigen. For example, as described herein, the conformation-specific antibody may specifically bind to the cis conformation of a phosphorylated or nonphosphorylated Xaa-Pro motif of a polypeptide (e.g., a Ser/Thr-Pro motif of a Pin1 substrate), but will not specifically bind to the trans conformation of the phosphorylated or nonphosphorylated Xaa-Pro motif of the polypeptide. In this case, the $K_d$ between the conformation-specific antibody and its antigen is, for example, at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M or greater. In addition to the binding specificity, the conformation-specific antibody will have, for example, at least 10- to 100-fold greater affinity to one conformation (e.g., the cis conformation) than to another conformation (e.g., the trans conformation) of the Xaa-Pro motif. The conformation-specific antibody may have, for example, at least $10^3$-, $10^4$-, $10^5$-, $10^6$-, $10^7$-, $10^8$-, $10^9$-, or $10^{10}$-fold greater affinity to one conformation (e.g., the cis conformation) than another conformation (e.g., the trans conformation).

Therapeutic Formulations

The conformation-specific antibodies of the present invention may be used in the treatment, inhibition, or prevention of disorders associated with the deregulation of PPIase (e.g., Pin1) activity. The conformation-specific antibodies may also be used to ameliorate symptoms of these disorders. Such disorders include, for example, cellular proliferation disorders (e.g., cancer), neurological disorders (e.g., Alzheimer's disease), aging-related disorders, asthma, microbial infections (e.g., viral infections (e.g., HIV infections)), and aging or other aging-related disorders.

The conformation-specific antibodies of the present invention can be formulated and administered in a variety of ways (e.g., routes known for specific indications, including, but not limited to, topically, orally, subcutaneously, bronchial injection, intravenously, intracerebrally, intranasally, transdermally, intraperitoneally, intramuscularly, intrapulmonary, vaginally, rectally, intraarterially, intralesionally, parenterally, intraventricularly in the brain, or intraocularly). For example, the pharmaceutical composition containing the conformation-specific antibody may be in the form of a pill, tablet, capsule, liquid, or sustained-release tablet for oral administration; a liquid for intravenous or subcutaneous administration; a polymer or other sustained-release vehicle for local administration; or an ointment, cream, gel, liquid, or patch for topical administration.

Continuous systemic infusion or periodic injection of the conformation-specific antibody can be used to treat or prevent a disorder. Treatment can be continued for a period of time ranging from one day through the lifetime of the subject, for example, 1 to 100 days, 1 to 60 days, or until the symptoms of the disorder are reduced or removed. Dosages vary depending on the severity of the disorder or symptoms of the disorder. Sustained-release systems and semipermeable, implantable membrane devices are also useful as a means for delivering the pharmaceutical composition of the invention. In another embodiment, the composition is administered locally, e.g., by inhalation, and this administration can be repeated periodically.

Therapeutic formulations are prepared using standard methods known in the art by mixing the active ingredient having the desired degree of purity with optional physiologically acceptable carriers, excipients, or stabilizers in the form of lyophilized formulations or aqueous solutions (see, e.g., Remington's Pharmaceutical Sciences, 20$^{th}$ edition, Ed. A. Gennaro, 2000, Lippincott, Williams & Wilkins, Philadelphia, Pa.). Acceptable carriers include, e.g., saline; buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagines, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at physiological concentrations. Optionally, the formulations of the invention can contain a pharmaceutically acceptable preservative. In some embodiments, the preservative concentration ranges from 0.1 to 2.0% v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant. Preferred surfactants are non-ionic detergents. Preferred surfactants include Tween-20 and pluronic acid (F68). Suitable surfactant concentrations are, e.g., 0.005 to 0.02%.

The conformation-specific antibodies of the invention are administered to the subject in therapeutically effective amounts. Preferably, the antibodies are administered parenterally or intravenously by continuous infusion. The dose and dosage regimen depends upon the severity of the disorder and the overall health of the subject. The amount of antibody administered is typically in the range of about 0.001 to about 10 mg/kg of subject weight, preferably 0.01 to about 5 mg/kg of subject weight.

For parenteral administration, the conformation-specific antibodies are formulated in a unit dosage injectable form (e.g., solution, suspension, or emulsion) in association with a pharmaceutically acceptable parenteral vehicle. Such vehicles are inherently non-toxic and non-therapeutic. Examples of such vehicles include, e.g., water, saline, Ringer's solution, dextrose solution, and 5% human serum albumin Nonaqueous vehicles, such as fixed oils and ethyl oleate, may also be used. Liposomes may be used as carriers. The vehicle may contain minor amounts of additives, such as substances that enhance isotonicity and chemical stability (e.g., buffers and preservatives). The antibodies typically are formulated in such vehicles at concentrations of about 1 mg/ml to 10 mg/ml.

The dosage required depends on the choice of the route of administration; the nature of the formulation; the nature of the subject's disorder; the subject's size, weight, surface area, age, and sex; other drugs being administered; and the judgment of the subject's physician. Wide variations in the needed dosage are to be expected in view of the variety of polypeptides and fragments available and the differing efficiencies of various routes of administration. For example, oral administration would be expected to require higher dosages than administration by intravenous injection. Variations in these dosage levels can be adjusted using standard empirical routines for optimization, as is well understood in the art. Administrations can be single or multiple (e.g., 2-, 3-, 6-, 8-, 10-, 20-, 50-, 100-, 150-, or more administrations). The composition can be administered at anytime (e.g., after diagnosis or detection of a disorder or a condition associated with the disorder (e.g., using the diagnostic methods known in the art or described herein) or before diagnosis of a disorder to a subject at risk of developing the disorder). Encapsulation of the antibody in a suitable delivery vehicle (e.g., polymeric microparticles or implantable devices) may increase the efficiency of delivery, particularly for oral delivery.

Where sustained release administration of the conformation-specific antibody is desired in a formulation with release characteristics suitable for the treatment of any disorder requiring administration of the antibody, microencapsulation of the antibody may be contemplated. Microencapsulation of polypeptides for sustained release has been successfully performed with human growth hormone (rhGH), interferon- (rhIFN-), interleukin-2, and MN rgp120 (see, e.g., Johnson et al., Nat. Med. 2: 795-799, 1996; Yasuda, Biomed. Ther. 27: 1221-1223, 1993; Hora et al., Bio/Technology 8: 755-758 1990; Cleland, "Design and Production of Single Immunization Vaccines Using Polylactide Polyglycolide Microsphere Systems," in "Vaccine Design: The Subunit and Adjuvant Approach," Powell and Newman, Eds., Plenum Press: New York, pp. 439-462, 1995; WO 97/03692; WO 96/40072; WO 96/07399; and U.S. Pat. No. 5,654,010, hereby incorporated by reference).

The sustained-release formulations may include those developed using poly-lactic-coglycolic acid (PLGA) polymer. The degradation products of PLGA, lactic and glycolic acids, can be cleared quickly from the human body. Moreover, the degradability of this polymer can be adjusted from months to years depending on its molecular weight and composition (see, e.g., Lewis, "Controlled release of bioactive agents from lactide/glycolide polymer," in M. Chasin and Dr. Langer (Eds.), Biodegradable Polymers as Drug Delivery Systems (Marcel Dekker: New York, pp. 1-41, 1990).

The antibody for use in the present invention may also be modified in a way to form a chimeric molecule comprising a conformation-specific antibody fused to another heterologous polypeptide or amino acid sequence, such as an Fc sequence or an additional therapeutic molecule (e.g., a chemotherapeutic agent).

The conformation-specific antibody of the present invention may be packaged alone or in combination with other therapeutic compounds as a kit. Non-limiting examples include, e.g., kits that contain, e.g., one pill, two pills, a powder (optionally in combination with a pill or tablet), a suppository and a liquid in a vial, or two topical creams. The kit can include optional components that aid in the administration of the unit dose to patients, such as vials for reconstituting powder forms, syringes for injection, customized IV delivery systems, or inhalers. Additionally, the unit dose kit can contain instructions for preparation and administration of the compositions. The kit may be manufactured as a single-use unit dose for one subject, multiple doses for a particular subject (e.g., at a constant dose or in which the individual compounds may vary in potency as therapy progresses), or the kit may contain multiple doses suitable for administration to multiple subjects (e.g., "bulk packaging"). The kit components may be assembled in cartons, blister packs, bottles, tubes, or vials.

Vaccine Compositions

The invention also features therapeutic and prophylactic vaccine compositions to confer passive immunity to a subject. The vaccine compositions of the present invention generally include one or more of the conformation-specific antibodies (e.g., humanized antibodies) described herein. Prophylactic vaccines can be used to reduce the likelihood of a subject acquiring a disorder associated with a deregulation of PPIase activity (e.g., Alzheimer's disease); therapeutic vaccines may be used to treat subjects diagnosed with such disorders. In one embodiment, the vaccine composition includes a conformation-specific antibody (e.g., a humanized antibody) that binds to the cis-pThr231-Pro motif of tau polypeptide. In another embodiment, the vaccine composition includes a conformation-specific antibody (e.g., a humanized antibody) that binds to the cis-pThr668-Pro motif of APP polypeptide.

The compositions can be administered in conjunction with an adjuvant, for example, cytokines, lymphokines, and chemokines (e.g., IL-2, GM-CSF, IL-12, γ-interferon, IP-10, MIP1β, and RANTES). When the vaccine compositions are used as therapeutic vaccines, the compositions can be administered in conjunction with known therapeutics.

The preparation of vaccine compositions containing one or more antibodies, antibody fragments, sFv molecules or combinations thereof, as the active ingredient is generally known to those of skill in the art. Typically, such vaccines are prepared as injectables (e.g., either as liquid solutions or suspensions or as solid forms suitable for solution or suspension in liquids prior to injection). The compositions will generally also include one or more pharmaceutically acceptable carriers. The vaccine compositions may be emulsified or the active ingredient (e.g., the conformation-specific antibody) may be encapsulated in a liposome. In addition, the vaccine compositions can be given as a single dose or as multiple dosages. The dosage regimen may be determined based on the particular needs of the subject to be treated.

Methods for preparing vaccine compositions for conferring passive immunity to a subject are described, for example, in WO 83/00229 and also reviewed in, e.g., Casadevall et al., *Nat. Rev. Microbiol.* 2:695-703 (2004); Bayry et al., *Trends Pharmacol. Sci.* 25:306-10 (2004); and Dunman et al., *Curr. Opin. Pharmacol.* 3:486-96 (2003), hereby incorporated by reference in their entirety.

Combination Therapies

The conformation-specific antibodies may be provided in conjunction (e.g., before, during, or after) with additional therapies to treat a disorder (e.g., a cellular proliferation disorder, a neurological disorder, asthma, or a microbial infection). Treatment therapies that can be used in combination with the methods of the invention include, but are not limited to, chemotherapeutic agents, anti-inflammatory agents, antimicrobial agents, analgesics and anesthetics, bronchodilators, agents for the treatment of neurological disorders, and PPIase inhibitors.

Chemotherapeutic Agents

Any suitable chemotherapeutic agent may be administered in combination with the conformation-specific antibody. Chemotherapeutic agents suitable for the composition described herein include, e.g., asparaginase, bleomycin, busulfan carmustine (BCNU), chlorambucil, cladribine (2-CdA), CPT11, cyclophosphamide, cytarabine (Ara-C), dacarbazine, daunorubicin, dexamethasone, doxorubicin (adriamycin), etoposide, fludarabine, 5-fluorouracil (5FU), hydroxyurea, idarubicin, ifosfamide, interferon-α (native or recombinant), levamisole, lomustine (CCNU), mechlorethamine (nitrogen mustard), melphalan, mercaptopurine, methotrexate, mitomycin, mitoxantrone, paclitaxel, pentostatin, prednisone, procarbazine, tamoxifen, taxol-related compounds, 6-thioguanine, topotecan, vinblastine, and vincristine. Exemplary chemotherapeutic agents are listed in, e.g., U.S. Pat. Nos. 6,864,275 and 6,984,654, hereby incorporated by reference.

Anti-Inflammatory Agents

Any suitable anti-inflammatory agent may be administered. Suitable anti-inflammatory agents include, e.g., nonsteroidal anti-inflammatory drugs (e.g., ibuprofen or tacrolimus), cyclooxygenase-2-specific inhibitors such as rofecoxib (Vioxx®) and celecoxib (Celebrex®), topical glucocorticoid agents, and specific cytokines directed at T lymphocyte function. Additional suitable anti-inflammatory agents include flubiprofen, diclofenac, and ketarolac. Anti-inflammatory concentrations known to be effective may be used. For example, ibuprofen may be present in the composition at concentrations sufficient to deliver between 25-800 mg per day to the subject. Exemplary anti-inflammatory agents are listed in, e.g., U.S. Pat. Nos. 7,112,578 and 7,199,119, hereby incorporated by reference.

Antimicrobial Agents

Any of the many known antimicrobial agents can be used in the compositions described herein at concentrations generally used for these agents. Antimicrobial agents include, e.g., antibacterials, antifungals, and antivirals.

Examples of antibacterial agents (e.g., antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, minocycline, and tetracycline), aminoglycosides (e.g., amikacin, gentamycin, kanamycin, neomycin, streptomycin, and tobramycin), macrolides (e.g., azithromycin, clarithromycin, and erythromycin), fluoroquinolones (e.g., ciprofloxacin, lomefloxacin, moxifloxacin, and norfloxacin), and other antibiotics including chloramphenicol, clindamycin, cycloserine, isoniazid, rifampin, and vancomycin. Exemplary antimicrobial agents are listed in, e.g., U.S. Pat. Nos. 6,830,745 and 7,056,917, hereby incorporated by reference.

Antiviral agents are substances capable of destroying or suppressing the replication of viruses. Examples of antiviral agents include 1-β-D-ribofuranosyl-1,2,4-triazole-3 carboxamide (ribavirin), 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir. Exemplary antiviral agents are listed in, e.g., U.S. Pat. Nos. 6,093,550 and 6,894,033.

Antifungal agents include both fungicidal and fungistatic agents, e.g., amphotericin B, butylparaben, clindamycin, econaxole, fluconazole, flucytosine, griseofulvin, nystatin, and ketoconazole. Exemplary antifungal agents are listed in, e.g., U.S. Pat. Nos. 5,627,153 and 7,125,842, hereby incorporated by reference.

Analgesics and Anesthetics

Any of the commonly used topical analgesics and anesthetics can be used as therapeutic agents in the invention. Examples of useful anesthetics include procaine, lidocaine, tetracaine, dibucaine, benzocaine, p-buthylaminobenzoic acid 2-(diethylamino) ethyl ester HCl, mepivacaine, piperocaine, and dyclonine Exemplary anesthetics are listed in, e.g., U.S. Pat. Nos. 6,562,363 and 6,569,839, hereby incorporated by reference.

Analgesics include opioids such as, e.g., morphine, codeine, hydrocodone, and oxycodone. Any of these analgesics may also be co-formulated with other compounds having analgesic or anti-inflammatory properties, such as acetaminophen, aspirin, codeine, naproxen, and ibuprofen. Exemplary analgesics are listed in, e.g., U.S. Pat. Nos. 6,869,974 and 7,202,259, hereby incorporated by reference.

Bronchodilators

Any commonly used bronchodilator can be used as a therapeutic agent in the invention described herein. Examples of useful bronchodilators include, e.g., pirbuterol, epinephrine, albuterol, salbutamol, salmeterol, or levalbuterol. Exemplary bronchodilators are listed in, e.g., U.S. Pat. Nos. 4,489,078, 4,591,588, 4,734,413, 6,299,863, and 6,555,583, hereby incorporated by reference.

Agents for the Treatment of Neurological Disorders

Agents for the treatment of neurological disorders may be used in combination with the therapeutic compositions described herein. Exemplary agents used for the treatment of such disorders include haloperidol, carbamazepine, valproate, donepezil, galanthamine, NMDA antagonists (e.g., memantine), PDE4 inhibitors (e.g., Ariflo), γ-secretase inhibitors, β-secretase inhibitors, GSK-3-α inhibitors, compounds which inhibit the aggregation of Aβ, carbidopa/levodopa, entacapone, tolcapone, pramipexole, ropinerole, pergolide, bromocriptine, selegeline, amantadine, vitamin E, amantadine, coenzyme Q, and anticholingergic agents.

PPIase Inhibitors

PPIase inhibitors include, for example, PiA (2,7-dimethylbenzophenanthroline-1,3,6,8(2H,7H)-tetrone), PiB (diethyl-1,3,6,8-tetrahydro-1,3,6,8-tetraoxobenzo-phenanthroline-2,7-diacetate), PiJ (diethyl-1,3,8,10-tetrahydro-1,3,8,10-tetraoxo-anthra[2,1,9-def:6,5,10-d'e'f']diisoquinoline-2,9-diacetate), cyclosporin A, FK506, ascomycin, and rapamycin. Additional PPIase inhibitors are described in U.S. Pat. No. 6,462,173 and U.S. Patent Application Publication No. 2004/0171019, hereby incorporated by reference.

Diagnostics

The present invention features methods and compositions to treat, diagnose, and monitor the progression of a disorder described herein (e.g., a cellular proliferation disorder, a neurological disorder, an aging-related disorder, asthma, or a microbial infection). The methods and compositions can include the detection and measurement of, for example, Pin1 substrates (or any fragments or derivatives thereof) containing a phosphorylated Ser/Thr-Pro motif in a cis or trans conformation. The methods can include measurement of absolute levels of the Pin1 substrate in a cis or trans conformation as compared to a normal reference. For example, a serum level of a Pin1 substrate in the cis or trans conformation that is less than 5 ng/ml, 4 ng/ml, 3 ng/ml, 2 ng/ml, or less than 1 ng/ml serum is considered to be predictive of a good outcome in a patient diagnosed with a disorder (e.g., a disorder associated with a deregulation of Pin1 activity). A serum level of the substrate in the cis or trans conformation that is greater than 5 ng/ml, 10 ng/ml, 20 ng/ml, 30 ng/ml, 40 ng/ml, or 50 ng/ml is considered diagnostic of a poor outcome in a subject already diagnosed with a disorder, e.g., associated with a deregulation of Pin1 activity.

For diagnoses based on relative levels of substrate in a particular conformation (e.g., a Pin1 substrate in the cis or trans conformation), a subject with a disorder (e.g., a disorder associated with a deregulation of PPIase activity) will show an alteration (e.g., an increase of 10%, 20%, 30%, 40%, 50%, 60%, 70%, 80%, 90%, or more) in the amount of the substrate in, for example, the cis conformation. A normal reference sample can be, for example, a prior sample taken from the same subject prior to the development of the disorder or of symptoms suggestive of the disorder, a sample from a subject not having the disorder, a sample from a subject not having symptoms of the disorder, or a sample of a purified reference polypeptide in a given conformation at a known normal concentration (i.e., not indicative of the disorder).

Standard methods may be used to measure levels of the substrate in any bodily fluid, including, but not limited to, urine, blood, serum, plasma, saliva, amniotic fluid, or cerebrospinal fluid. Such methods include immunoassay, ELISA, Western blotting, and quantitative enzyme immunoassay techniques.

For diagnostic purposes, the conformation-specific antibodies may be labeled. Labeling of the antibody is intended to encompass direct labeling of the antibody by coupling (e.g., physically linking) a detectable substance to the antibody, as well as indirect labeling the antibody by reacting the antibody with another reagent that is directly labeled. For example, the antibody can be labeled with a radioactive or fluorescent marker whose presence and location in a subject can be detected by standard imaging techniques.

The diagnostic methods described herein can be used individually or in combination with any other diagnostic method described herein for a more accurate diagnosis of the presence or severity of a disorder (e.g., a cellular proliferation disorder or a neurological disorder). Examples of additional methods for diagnosing such disorders include, e.g., examining a subject's health history, immunohistochemical staining of tissues, computed tomography (CT) scans, or culture growths.

Subject Monitoring

The diagnostic methods described herein can also be used to monitor the progression of a disorder (e.g., a cellular proliferation disorder or a neurological disorder) during therapy or to determine the dosages of therapeutic compounds. In one embodiment, the levels of, for example, polypeptides (e.g., Pin1 substrates) with pSer/Thr-Pro motifs in the cis or trans conformation are measured repeatedly as a method of diagnosing the disorder and monitoring the treatment or management of the disorder. In order to monitor the progression of the disorder in a subject, subject samples can be obtained at several time points and may then be compared. For example, the diagnostic methods can be used to monitor subjects during chemotherapy. In this example, serum samples from a subject can be obtained before treatment with a chemotherapeutic agent, again during treatment with a chemotherapeutic agent, and again after treatment with a chemotherapeutic agent. In this example, the level of Pin1 substrate with a pSer/Thr-Pro motif in the cis conformation in a subject is closely monitored using the conformation-specific antibodies of the invention and, if the level of Pin1 substrate with a pSer/Thr-Pro motif in the cis conformation begins to increase during therapy, the therapeutic regimen for treatment of the disorder can be modified as determined by the clinician (e.g., the dosage of the therapy may be changed or a different therapeutic may be administered). The monitoring methods of the invention may also be used, for example, in assessing the efficacy of a particular drug or therapy in a subject, determining dosages, or in assessing progression, status, or stage of the infection.

EXAMPLES

Example 1. Synthesis of Conformation-Specific Antibodies

We describe the synthesis and purification of conformation-specific antibodies recognizing cis- or trans-pT231-P tau.

Figure 3:
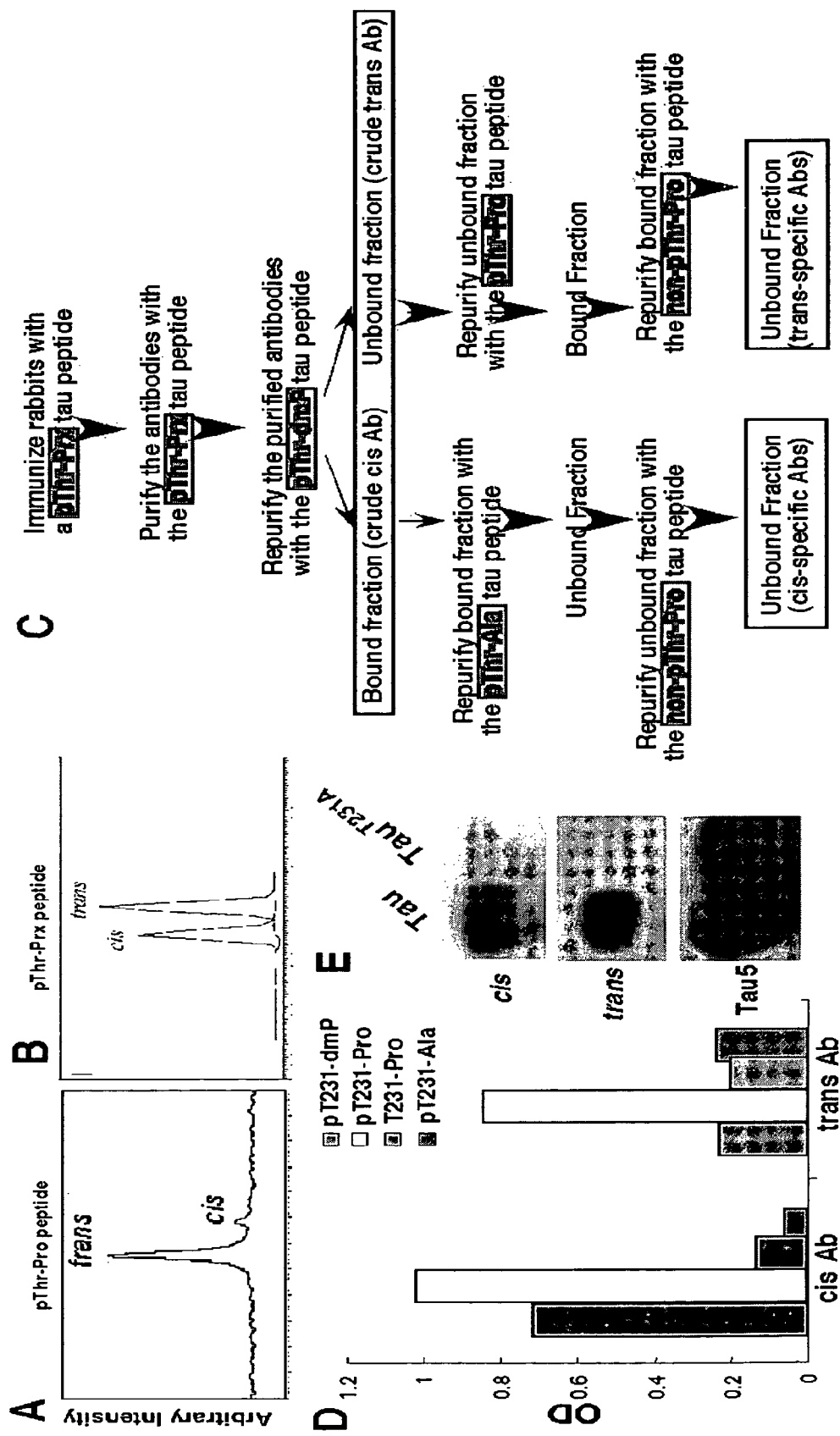
FIGS. 3A and 3B are graphs showing the cis/trans content of a pThr-Pro peptide and pThr-Prx peptide, respectively.
FIG. 3C is a schematic diagram showing the methodology for producing conformation-specific antibodies.
FIG. 3D is a bar graph showing that only cis-specific antibodies recognized pT231-dmP tau peptide, assayed by ELISA. Both cis- and trans-specific antibodies recognized pT231-Pro tau peptide. Neither the cis- or trans-specific antibodies recognized nonphosphorylated tau peptide or pT231-Ala tau peptide.
FIG. 3E is a series of Western blots that show that both cis- and trans-specific antibodies recognized pT231-Pro-containing tau protein, but not Ala231-Pro-containing tau protein.

Since about 90% of pSer/Thr-Pro motifs in a synthetic peptide are in trans (FIG. 3A), a major challenge is to increase the cis content in the antigen. We have identified a non-natural amino acid that has a similar structure to proline, homoproline (PIP). PIP dramatically increases the cis content of the synthetic peptide to about 50% (FIGS. 3A and 3B). Peptides containing PIP or similar proline analogs (e g, dmP) are synthesized according to standard techniques. These peptides are fragments of full-length phosphorylated proteins (e.g., Pin1 substrates) containing Xaa-Pro motifs (e.g., tau protein or APP) with the proline of the Xaa-Pro motif of the full-length polypeptide replaced by a proline analog in the synthetic peptide. These peptides are used to immunize host animals (e.g., rabbits). See, e.g., FIG. 3C.

To separate cis- and trans-specific antibodies generated by the immunized animals, we synthesized a biotinated pT231-(L-5,5-dimethylproline) (dmP) tau peptide and conjugated it to an affinity column and purify the cis- and trans-specific antibodies according to the scheme in FIG. 3C. Importantly, the cis-specific antibodies, but not trans-specific antibodies, recognize the pT231-dmP tau peptide (FIG. 3D). Thus, the pT231-dmP column bound cis-specific antibodies, while trans-specific antibodies were found in the unbound fraction. The cis-specific antibody was eluted from the column using a Thr-Pro peptide. To obtain purified trans-specific antibody, the unbound fraction containing the trans-specific antibody was repurified with a pThr-Pro peptide, as trans-specific antibody binds pThr-Pro.

We found that both cis- and trans-specific tau antibodies recognized pT231-Pro tau peptide with similar intensity (FIG. 3D). Neither cis- nor trans-specific antibodies recognized the nonphosphorylated T231-Pro tau peptide or pT231-Ala tau peptide. Moreover, both cis- and trans-specific antibodies specifically recognized phosphorylated T231-containing tau protein, but not its Thr231Ala point mutant. Thus, cis- and trans-specific pT231 tau antibodies have the expected properties and specificity with little cross-reactivity.

Figure 4:
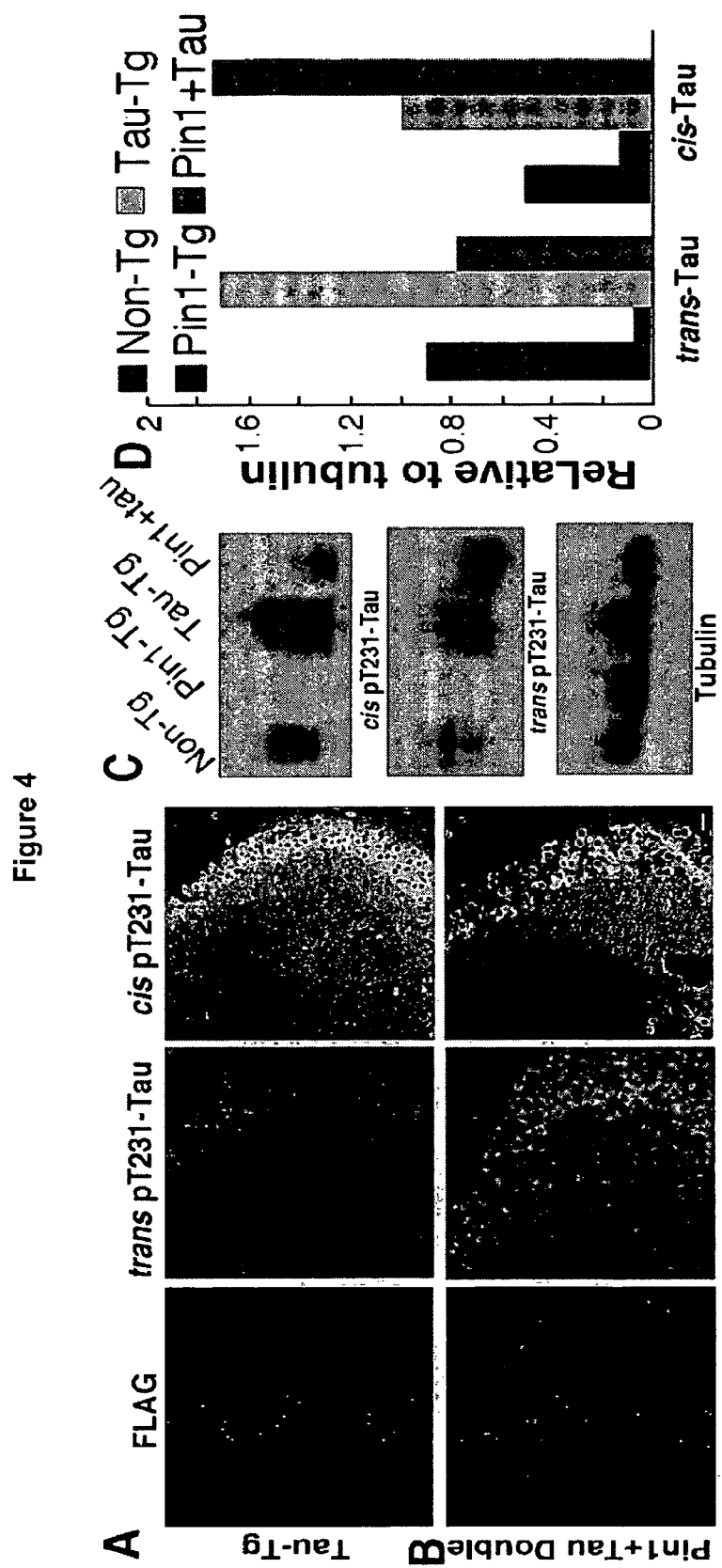
FIGS. 4A and 4B are micrographs showing that the cis-, but not trans-, pT231-tau accumulated during tauopathy development, but is effectively reversed by Pin1 overexpression in mouse models.
FIG. 4C is a series of Western blots that show that Pin1 overexpression in tau mice decreases the cis content, but increases the trans content, reversing the cis/trans ratio. The semiquantitative results of the Western blots are shown in FIG. 4D.

Example 2. Pin1 Overexpression Decreased Cis-pT231-Tau, but Increased Trans-pT231-Tau in Tau-Tg Mice We found that the cis/trans ratio of pT231-tau increases during tauopathy development, but that overexpression of Pin1 can reduce the amount of tau peptide that is in the cis conformation. An AD mouse model overexpressing human wild-type tau under the Thy1 promoter (Tau-Tg) develops an age-dependent tauopathy phenotype. We found that only the cis, but not trans, pT231-Tau were dramatically accumulated in aged brains (FIGS. 4A, C, and D). However, when Tau-Tg mice were crossed with Thy1-Pin1 transgenic mice, which reduced endogenous tau levels (FIGS. 4C and D). Pin1 overexpression not only effectively prevented accumulation of cis pT231-Tau, but also increased trans, pT231-Tau (FIGS. 4B, C, and D), as documented both by immunostaining and immunoblotting analyses. These conformation-specific results provide the first in vivo evidence that Pin1 promotes cis-to-trans isomerization of pTau to protect against tangle formation. These results also suggest that it is not general pT231-Tau, but rather its cis/trans ratio, that is pathologically significant in the tauopathy development in mouse models.

Example 3. Elevation of Cis-, but not Trans-, pT231-Tau in Degenerated Human Brains We found that cis-, but not trans-, pT231-tau is elevated in subjects with mild cognitive impairment (MCI) and AD.

Figure 5:
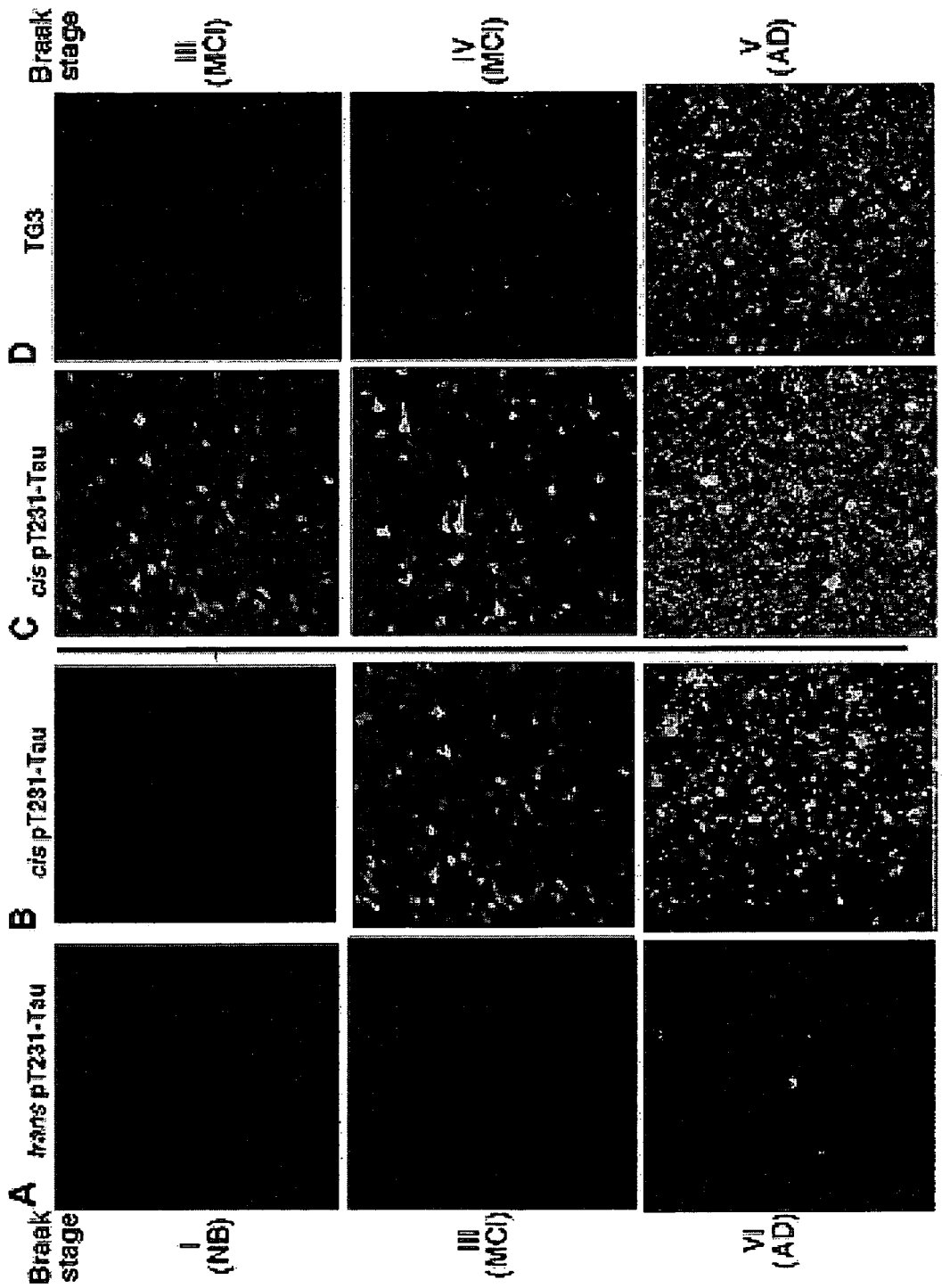
FIG. 5 is a series of micrographs showing that cis-, but not trans-, pT231-tau is elevated in human brain samples with mild cognitive impairment (MCI) and further accumulates as AD progresses.
Figure 6:
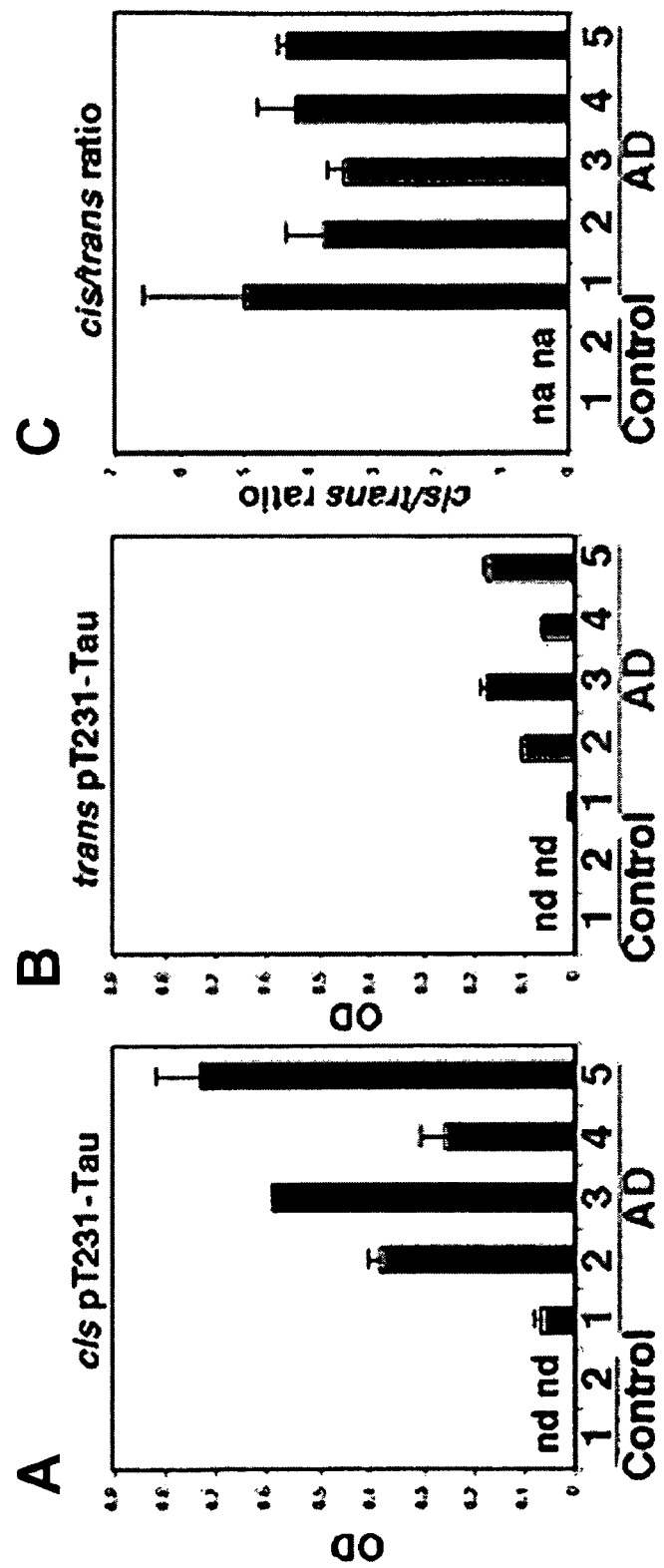
FIG. 6 is a series of bar graphs showing that the cis/trans ratio of pT231-tau in cerebrospinal fluid (CSF) was elevated in advanced AD patients with small individual variations. The cis- and trans-pT231-tau in CSF of late AD patients and controls were assayed in triplicate by ELISA using cis- (FIG. 6A) or trans- (FIG. 6B) specific antibodies.

To examine changes in pT231-tau conformation at different AD stages in humans, we immunostained normal and AD brain tissue with cis- or trans-specific tau antibodies. There was little cis- or trans-pT231-tau present in normal human brains (FIGS. 5A and 5B). In AD, trans-pT231-tau was barely detectable. Even at Braak VI, very few neurons displayed a strong trans-pT231-tau signal (FIG. 5A). In contrast, cis-pT231-tau was detected and found to accumulate in somatodendritic regions of neurons at Braak III or IV (MCI) brain tissue (FIG. 5B). Furthermore, cis-pT231-tau continued to accumulate as Braak stage increased (FIGS. 5B and 5C). These results showed that cis-pT231-tau is accumulated at an early stage of degeneration before AD pathologies develop.

To confirm these results, we compared brain tissue immunostained with either cis-pT231-tau antibodies or mAb TG3. Brain tissue immunostained with TG3 showed strong signals only in Braak stage V AD brain tissue, but not in Braak III or IV MCI brain tissue (FIG. 5D), confirming that TG3 recognizes tau phosphorylated on T231 only in the AD-specific conformation. However, cis-pT231-tau was readily detected in Braak III or IV MCI brain tissue (FIG. 5D). These results show that cis-, but not trans-, pT231-tau is elevated at very early stages of AD and further accumulates as the disease progresses in human brains.

Example 4. The Cis/Trans Ratio of pT231-Tau in the Cerebrospinal Fluid (CSF) of AD Patients We found that the cis/trans ratio of pT231-tau in the cerebrospinal fluid (CSF) was elevated in late AD patients with small individual variations.

To examine whether it is possible to assay cis- and/or trans-pT231-tau in CSF, we obtained postmortem CSF from five late AD patients and two control subjects (courtesy of Dr. Neil Kowall) and performed an assay using the INNOTEST hTau ELISA kit (Innogenetics) to detect the presence of cis- and trans-pT231-tau. The detection antibodies in the kit were replaced with cis- or trans-pT231-tau polyclonal antibodies. Although neither cis- nor trans-pT231-tau was detectable in control CSF, cis- and trans-pT231-tau were detected in the CSF of AD patients (p<0.0001) and showed large individual variations. However, variations in the cis/trans ratio values of pT231-tau were smaller (from >10-fold to <0.5-fold). These results show that, unlike the pT231-tau peptide (FIG. 3D), the cis- and trans-pT231-tau present in CSF do not have the same immunoreactivity to the cis and trans antibodies, indicating the feasibility of quantifying cis- and trans-pT231-tau proteins in CSF. These preliminary results show that both cis- and trans-pT231-tau proteins are elevated in the CSF of AD patients and suggest that cis/trans ratio of pT231-tau can serve as a biomarker for AD.

Example 5. Monoclonal Antibodies Recognizing Cis- and Trans-pT231-Tau

To establish cis- and trans-pT231-tau conformations as biomarkers for AD diagnosis, it is important to produce monoclonal antibodies that distinguish cis- and trans-pT231-Pro motif in tau. We immunize rabbits with pT231-Prx tau peptide (KVAVVR-(pT231)-(Prx)-PKSPS) and screen hybridoma clones producing antibodies recognizing pT231-tau in the cis or trans conformation using various in vitro and in vivo procedures known to one of skill in the art.

Example 6. Levels of Cis- and Trans-pT231-Tau in Brain Tissue and CSF at Different Stages of AD Human AD brain tissue samples and normal controls are obtained from brain autopsy and ventricular CSF samples collected from the patients with Braak I-VI stage disease. The levels of cis- and trans-pT231-tau in CSF samples are measured using INNOTEST hTau ELISA kit (Innogenetics), replacing the detection antibody with cis- and trans-pT231-tau polyclonal antibodies or mAb. A pT231-tau synthetic peptide is used as a standard. Simultaneous measurement of t-tau, pT231-tau, and Aβ1-42 in CSF has been well established using the multiplex xMAP Luminex platform with Innogenetics' immunoassay kit-based reagents (INNO-BIA AlzBio3; Ghent, Belgium). Alternatively, it is possible to replace the pT231 detection antibody CP9 with cis- and trans-specific antibodies to simultaneously measure cis- and trans-pT231-tau levels with t-tau and Aβ1-42. Calibration curves are produced for each biomarker using aqueous buffered solutions that contain the combination of three biomarkers at different concentrations of recombinant tau, synthetic Aβ1-42 peptide, and pT231-tau synthetic peptide as standards. Assays are carried out in triplicate for each sample and the OD values imported into SPSS analytical software and transformed into concentrations according to the standard curve for statistical analysis.

To understand the relationship between pT231-tau conformations in CSF and in brain tissue, ELISA is used to quantify cis- and trans-pT231-tau levels in brain lysates Immunostaining and immunoblotting analyses are performed on frontal cortex tissues from the same individuals whose CSF samples are analyzed to confirm the ELISA results. To examine the relationship between pT231-tau conformations and other tau-related pathologies, the relationship between cis- and trans-pT231-tau and the presence of the pretangle pathology and/or neurofibrillary lesion is determined. The pretangle pathology is detected by immunostaining brain sections with various phospho-specific and/or conformation-specific tau antibodies or by extracting tau from brains using sarcosyl, followed by immunoblotting analysis with various tau antibodies. The presence of neurofibrillary lesions and neurodegeneration is detected by Gallyas silver staining, thioflavin-S staining, NeuN staining, and Nissl staining. To compare the changes of tau conformations and their relationship with other tauopathy phenotypes at different Braak stages, immunoblotting data is quantified with imagequant or immunofluoresence staining, using Zeiss LSM510 META imaging system and software for statistically relevant analysis. A comparative study of cis- and trans-pT231-tau, pT231-tau, total tau, and Aβ1-42 levels at various Braak stages, among AD and other different dementia groups, or among other quantitative measures of AD progression (such as age-at-onset (AAO), disease duration, and Mini-Mental State Examination (MMSE) score) is completed by using Student t test or by one-way analysis of variance followed by Bonferroni post hoc test when multiple comparisons are performed. All data analyses are performed with statistical software.

OTHER EMBODIMENTS

From the foregoing description, it will be apparent that variations and modifications may be made to the invention described herein to adopt it to various usages and conditions. Such embodiments are also within the scope of the following claims.

All publications, patent applications, and patents mentioned in this specification are herein incorporated by reference to the same extent as if each independent publication, patent application, or patent was specifically and individually indicated to be incorporated by reference.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. A method of generating a conformation-specific antibody or fragment thereof that specifically binds to a Xaa-Pro motif of the naturally occurring form of a polypeptide, where Xaa is any amino acid residue, said method comprising:
   (i) administering a proline-analog-containing antigenic peptide to a non-human host animal, said antigenic peptide comprising a Xaa-Pro motif comprising said proline analog;
   (ii) isolating antisera containing said antibody or fragment thereof produced in said animal; and
   (iii) purifying said conformation-specific antibody or fragment thereof from said antisera; wherein said conformation-specific antibody or fragment thereof specifically binds to the Xaa-Pro motif of the naturally occurring form of said polypeptide;
   wherein said proline analog is selected from the group consisting of homoproline, azetidine-2-carboxylic acid (Aze), tert-butyl-L-proline (TBP), trans-4-fluoro-L-proline (t-4F-Pro), and cis-4-fluoro-L-proline (c-4F-Pro), and wherein the peptidyl-prolyl bond of said Xaa-Pro motif of said antigenic peptide is in a cis conformation, or is in a trans conformation.

2. The method of claim 1, wherein said Xaa is serine or threonine.

3. The method of claim 1, wherein said Xaa is phosphorylated.

4. The method of claim 1, wherein said Xaa is not phosphorylated.

5. The method of claim 1, wherein the peptidyl-prolyl bond of said Xaa-Pro motif of said antigenic peptide is in a cis conformation.

6. The method of claim 5, wherein said antibody or fragment thereof binds to the cis conformation of said Xaa-Pro motif of said polypeptide with at least 10- to 100-fold greater affinity than to the trans conformation of said Xaa-Pro motif of said polypeptide.

7. The method of claim 1, wherein the peptidyl-prolyl bond of said Xaa-Pro motif of said antigenic peptide is in a trans conformation.

8. The method of claim 7, wherein said antibody or fragment thereof binds to the trans conformation of said Xaa-Pro motif of said polypeptide with at least 10- to 100-fold greater affinity than to the cis conformation of said Xaa-Pro motif of said polypeptide.

9. The method of claim 1, wherein said polypeptide is a peptidyl-prolyl cis/trans isomerase (PPlase) substrate.

10. The method of claim 9, wherein said PPlase substrate is a Pin1 substrate.

11. The method of claim 10, wherein said Pin1 substrate is NIMA, RAB4, CDC25, WEE1, PLK1, MYT1, CDC27, CENP-F, Incenp, RBP1, NHERF-1, KRMP1, CK2, TopoIIα, DAB2, p54nrb, Sil, EMI1, cyclin D1, Ki67, c-Myc, cyclin E, c-Jun, β-catenin, Cf-2, NF-κB, RAF1, C-Fos, RARα, AIB1/SRC-3, HBx, STAT3, p53, Bcl-2, p73, BimEL, $p66^{Shc}$, CHE1, tau, amyloid precursor protein (APP), APP fragment, synphilin-1, gephyrin, MCL1, NFAT, AUF1, IRF3, BTK, SIN3-RPD3, or hSpt5.

12. The method of claim 1, wherein the peptidyl-prolyl bond of said Xaa-Pro motif of said antigenic peptide is fixed in the cis conformation or the trans conformation.

13. The method of claim 1, wherein said antigenic peptide is at least 8 amino acid residues in length.

14. The method of claim 13, wherein said antigenic peptide is between 8 and 20 amino acid residues in length.

15. The method of claim 1, wherein said conformation-specific antibody is a monoclonal antibody.

16. The method of claim 1, wherein said conformation-specific antibody is a polyclonal antibody.

17. The method of claim 1, wherein said host animal is a rabbit.

18. The method of claim 1, wherein said host animal is a bovine, equine, canine, ovine, feline, goat, sheep, or chicken.

19. The method of claim 1, wherein the conformation-specific antibody specifically binds to the cis conformation of said Xaa-Pro motif of said polypeptide with a Kd of at least about $10^{-4}$ M or greater, or wherein the conformation-specific antibody specifically binds to the trans conformation of said Xaa-Pro motif of said polypeptide with a Kd of at least about $10^{-4}$ M or greater.

20. The method of claim 1, wherein Xaa is serine or threonine and wherein said polypeptide is a peptidyl-prolyl cis/trans isomerase (PPlase) substrate.

* * * * *

```
                        SEQUENCE LISTING

<160> NUMBER OF SEQ ID NOS: 2

<210> SEQ ID NO 1
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 1

Val Asp Ala Ala Val Thr Pro Glu Glu Arg His Leu Ser Lys
1               5                   10

<210> SEQ ID NO 2
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 2

Lys Val Ala Val Val Arg Thr Pro Pro Lys Ser Pro Ser
1               5                   10
```